US006399826B1

(12) United States Patent
Senanayake et al.

(10) Patent No.: US 6,399,826 B1
(45) Date of Patent: Jun. 4, 2002

(54) SALTS OF SIBUTRAMINE METABOLITES, METHODS OF MAKING SIBUTRAMINE METABOLITES AND INTERMEDIATES USEFUL IN THE SAME, AND METHODS OF TREATING PAIN

(75) Inventors: Chrisantha Hugh Senanayake, Shrewsbury; Qun Kevin Fang, Wellesley; Zhengxu Han, Shrewsbury; Dhileepkumar Krishnamurthy, Westboro, all of MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/480,889

(22) Filed: Jan. 11, 2000

Related U.S. Application Data

(63) Continuation-in-part of application No. 09/372,158, filed on Aug. 11, 1999.

(51) Int. Cl.[7] .............................................. C07C 249/00
(52) U.S. Cl. ........................ 564/271; 564/302; 564/304
(58) Field of Search ................................ 564/271, 302, 564/304

(56) References Cited

U.S. PATENT DOCUMENTS

| | | | |
|---|---|---|---|
| 3,155,669 A | 11/1964 | Janssen et al. | |
| 3,155,670 A | 11/1964 | Janssen et al. | |
| 3,471,515 A | 10/1969 | Troxler et al. | |
| 3,536,809 A | 10/1970 | Applezweig | 424/28 |
| 3,598,123 A | 8/1971 | Zaffaroni | 128/268 |
| 3,845,770 A | 11/1974 | Theeuwes et al. | 128/260 |
| 3,916,899 A | 11/1975 | Theeuwes et al. | 128/260 |
| 3,960,891 A | 6/1976 | Malen et al. | |
| 4,008,719 A | 2/1977 | Theeuwes et al. | 128/260 |
| 4,522,828 A | 6/1985 | Jeffery et al. | |
| 4,552,828 A | 11/1985 | Toya et al. | |
| 4,746,680 A | 5/1988 | Jeffery et al. | |
| 4,806,570 A | 2/1989 | Jeffery et al. | |
| 4,814,352 A | 3/1989 | Jeffery et al. | 514/646 |
| 4,816,488 A | 3/1989 | Rees | 514/646 |

(List continued on next page.)

FOREIGN PATENT DOCUMENTS

| | | |
|---|---|---|
| DE | 32 12 682 A1 | 10/1982 |
| EP | 0 035 597 | 9/1981 |
| EP | 0 781 561 A1 | 7/1997 |
| GB | 2098602 A | 11/1982 |
| WO | 88/06444 | 9/1988 |
| WO | 90/06110 | 6/1990 |
| WO | 94/00047 | 1/1994 |
| WO | 94/00114 | 1/1994 |
| WO | WO 94/28902 | 12/1994 |
| WO | 95/20949 | 8/1995 |
| WO | 95/21615 | 8/1995 |
| WO | WO 97/03675 | 2/1997 |
| WO | 97/20810 | 6/1997 |
| WO | WO 98/06722 | 2/1998 |
| WO | 98/11884 | 3/1998 |

(List continued on next page.)

OTHER PUBLICATIONS

Baldessarini et al., *Life Science* 39: 1765–1777, (1986).
Buckett et al., "BTS 54 524—An Approach to Rapidly Acting Antidepressant," *New Concepts in Depression* 2: 167–172 (1988).
Buckett et al., "Sibutramine Hydrochloride," *Drugs of the Future* 13(8): 736–738 (1988).
Carstensen, J., *Drug Stability: Principles & Practice*, 2d. Ed., pp. 379–380, Marcel Dekker, NY, NY, (1995).
*Diagnostic and Statistical Manual of Mental Disorders*, Fourth Ed., American Psychiatric Association, (1997).
*Diagnostic and Statistical Manual of Metal Disorders*, 3rd Ed., American Psychiatric Association (1981).
Eliel, E.L., *Sterochemistry of Carbon Compounds* (McGraw–Hill, NY, 1962).
Evans et al., "Prevalence of Alzheimer's Disease in a Community Population of Older Persons," *J.A.M.A.* 262: 2551–2556 (1989).
Fuentes, J. et al., "Comparison of the apparent anti–depressant activity of (−) and (+) tranylpromine in an animal model", *Chemical Abstracts*, 85: 7, p. 31, No. 40768t (1976).
*Introduction to Pharmaceutical Dosage Forms*, 4th ed., Lea & Febiger, Philadelphia (1985).
Jacques et al., "Enantiomers, Racemates and Resolutions," (Wiley–Interscience, NY, 1981).
Jamali et al., *Journal of Pharmaceutical Sciences*, 78: 9: 695–715 (1989).
Kula et al., "Effects of N–Substituted Phenyltetrahydropyridines on Cerebral High–Affinity Synatosamal Uptake of Dopamine and Other Monoamines in Several Mammalian Species," *Life Sciences* 34(26): 2567–2575, (1984).
The Merck Manual of Diagnosis and Therapy, 17th Ed., Merck & Co., Inc., Whitehouse Station, NJ, (1999).
*Remington's Pharmaceutical Sciences*, 18th ed., Mack Publishing, Easton PA (1990).
*Remington's Pharmaceutical Sciences*, 16th ed., Mack Publishing, Easton PA (1980).
U.S. Pharmocopia (USP) SP (XXI)/NF (XVI).
Wilen et al., *Tetrahedron*, 2725–36 33(21) (1977).
Wilen, S.H., Tables of Resolving Agents and Optical Resolutions 268 (E.L. Eliel ed., Univ. of Notre Dame Press, Notre Dame, IN, 1972).
Buckett et al., The Pharmacology of Sibutramine Hydrochloride (BTS 54 524), A New Antidepressant Which Induces Rapid Noradrenergic Down–Regulation, Prog. Neuro–psychopharm. & Biol. Psychiat., 12:575–584, 1988.

(List continued on next page.)

*Primary Examiner*—Samuel Barts
(74) *Attorney, Agent, or Firm*—Pennie & Edmonds LLP

(57) ABSTRACT

Methods of making and using racemic and optically pure metabolites of sibutramine, and pharmaceutically acceptable salts, solvates, and clathrates thereof, are disclosed. Pharmaceutical compositions and dosage forms are also disclosed which comprise a dopamine reuptake inhibitor, such as a racemic or optically pure sibutramine metabolite, and optionally an additional pharmacologically active compound.

5 Claims, No Drawings

U.S. PATENT DOCUMENTS

| | | | |
|---|---|---|---|
| 4,871,774 A | 10/1989 | Rees | |
| 4,929,629 A | 5/1990 | Jeffery | |
| 4,939,175 A | 7/1990 | Ukai et al. | |
| 4,988,814 A | 1/1991 | Abou-Gharbia et al. | |
| 5,059,595 A | 10/1991 | Le Grazie | 424/468 |
| 5,068,440 A | 11/1991 | Jeffery et al. | |
| 5,073,543 A | 12/1991 | Marshall et al. | 514/21 |
| 5,104,899 A | 4/1992 | Young et al. | 514/646 |
| 5,120,548 A | 6/1992 | McClelland et al. | 424/473 |
| 5,250,534 A | 10/1993 | Bell et al. | 514/258 |
| 5,354,556 A | 10/1994 | Sparks et al. | 424/419 |
| 5,436,272 A | 7/1995 | Scheinbaum | |
| 5,459,164 A | 10/1995 | Vargas | |
| 5,552,429 A | 9/1996 | Wong et al. | |
| 5,591,767 A | 1/1997 | Mohr et al. | 514/413 |
| 5,639,476 A | 6/1997 | Oshlack et al. | 424/468 |
| 5,674,553 A | 10/1997 | Shinoda et al. | 427/68 |
| 5,719,283 A | 2/1998 | Bell et al. | 544/262 |
| 5,733,566 A | 3/1998 | Lewis | 424/426 |
| 5,780,051 A | 7/1998 | Eswara et al. | |
| 5,795,880 A | 8/1998 | Svec et al. | |
| 6,127,363 A | 10/2000 | Diherty et al. | 514/220 |

FOREIGN PATENT DOCUMENTS

| | | |
|---|---|---|
| WO | 98/13033 | 4/1998 |
| WO | 98/13034 | 4/1998 |
| WO | 99/33450 | 7/1999 |

OTHER PUBLICATIONS

Butler, D., Facile Cycloalkylation of Arylacetonitriles in Dimethyl Sulfoxide, J. Org. Chem., 36:1308–1309 (1971).

Cananne, P., et al., Effet du Benzene Dans la Reaction de Grignard sur les Nitriles, Tetrahedron Lett., 21:155–58 (1980).

Castello, R.A. et al., Discoloration of Tables Containing Amines and Lactose, Pharm. Sci. 51(2):106–108 (1962).

Cheetham, S.C., et al., [$^3$H]Paroxetine Binding in Rat Frontal Cortex Strongly Correlates with [$^3$H]5–HT Uptake: Effect of Administration of Various Antidepressant Treatments, Neuropharmacology (1993), 32(8), 737–743.

Cliffe et al., (S)–N–tert–Butyl–3–(4–(2– methoxyphenyl)–piperazin–1–yl)–2–phenylpropanamide [(S)–WAY–100135]: A Selective Antagonist at Presynaptic and Postsynaptic 5–HT$_{1A}$ Receptors, Med. Chem., 36:1509–1510 91993).

Dreshfield et al., Enhancement of Fluoxetine–Dependent Increase of Extracellular Serotonin (5–HT) Levels by (–)–Pindolol, an Antagonist at 5–HT $_{1A}$ Receptors, Neurochem. Res., 21(5):557–562 (1996).

Goodman & Gilman, The Pharmacological Basis of Therapeutics, 362–373, 404 (9$^{th}$ ed. McGraw–Hill, 1996).

Gray, A.M., et al., The Involvement of the Opioidergic System in the Antiociceptive Mechanism of Action of Antidepressant Compounds, BR.J. Pharmacol., vol. 124, No. 4, (1998) pp 669–674.

Handbook of Pharmaceutical Excipients, 2$^{nd}$ ed., Wade and Willer eds., pp. 257–259 (1994).

Heal, D.J., et al., A Comparison of the Effects on Central 5–HT Function of Sibutramine Hydrochloride and Other Weight–Modifying Agents, BR.J. Pharmacol. (1998), 125(2), 301–308.

Hillver et al., (S)–5–Fluoro–8–hydroxy–2–(dipropylamino)tetralix: A Putative %–HT $_{1A}$ receptor Antagonist, J. Med. Chem., 33:1541–44 (1990).

J. Med. Chem., vol. 36, No. 17, 2540 (1993).

Jeffery, J.E., et al., Synthesis of Sibutramine, A Novel Cyclobutylalkylamine Useful in the Treatment of Obesity, and its Major Human Metabolites, J. Chem. Soc. Perkin. Trans. 1, 2583–2589 (1996).

King et al., Clinical Pharmacology of Sibutramine Hydrochloride (BTS 54524), A New Antidepressant, in Healthy Volunteers, Br. J. Clin. Pharm., 26(5):607–611 (1988).

Luscombe, G.P., et al., The Contribution of Metabolites to the rapid and Potent Down–Regulation of Rat Cortical β–Adrenoceptors by the Putative Antidepressant Sibutramine Hydrochloride, Neuropharmacology, vol. 28, No. 2, (1989) pp 129–134.

Middlemiss et al., Centrally Active 5–HT Receptor Agonists and Antagonists, Neurosci. and Biobehv. Rev., 16:75–82 (1992).

Moreau et al., Behavioral Profile of the 5–HT $_{1A}$ Receptor Antagonist (S)–UH–301 in Rodents and Monkeys, Brain Res. Bull., 29:901–04 (1992).

Nakada, Y., et al., An Enantioconvergent Route to (–)–Kainic Acid, Tetrahadron Lett., 38:857–860 (1997).

Physician's Desk Reference® 2520 (52$^{nd}$ ed., 1998).
Physician's Desk Reference® 2958 (52$^{nd}$ ed., 1998).
Physician's Desk Reference® 473–475 (53$^{rd}$ ed., 1999).
Physician's Desk Reference® 475–476 (53$^{rd}$ ed., 1999).
Physician's Desk Reference® 764–766 (53$^{rd}$ ed., 1999).
Physician's Desk Reference® 823–825 (53$^{rd}$ ed., 1999).
Physician's Desk Reference® 978–979 (53$^{rd}$ ed., 1999).
Physician's Desk Reference® 1054–1056 (53$^{rd}$ ed., 1999).
Physician's Desk Reference® 1332–1334 (53$^{rd}$ ed., 1999).
Physician's Desk Reference® 1369–1370 (53$^{rd}$ ed., 1999).
Physician's Desk Reference® 1432–1436 (53$^{rd}$ ed., 1999).
Physician's Desk Reference® 1494–1498 (53$^{rd}$ ed., 1999).
Physician's Desk Reference® 1641–1645 (53$^{rd}$ ed., 1999).
Physician's Desk Reference® 2004–2009 (53$^{rd}$ ed., 1999).
Physician's Desk Reference® 2075–2078 (53$^{rd}$ ed., 1999).
Physician's Desk Reference® 2190–2192 (53$^{rd}$ ed., 1999).
Physician's Desk Reference® 2367–2368 (53$^{rd}$ ed., 1999).
Physician's Desk Reference® 2396–2399 (53$^{rd}$ ed., 1999).
Physician's Desk Reference® 2490–2493 (53$^{rd}$ ed., 1999).
Physician's Desk Reference® 2516–2521 (53$^{rd}$ ed., 1999).
Physician's Desk Reference® 2688–2691 (53$^{rd}$ ed., 1999).
Physician's Desk Reference® 2701–2704 (53$^{rd}$ ed., 1999).
Physician's Desk Reference® 2720–2726 (53$^{rd}$ ed., 1999).
Physician's Desk Reference® 2735–2736 (53$^{rd}$ ed., 1999).
Physician's Desk Reference® 2886–2888 (53$^{rd}$ ed., 1999).
Physicain's Desk Reference® 2908–2910 (53$^{rd}$ ed., 1999).
Physician's Desk Reference® 3092–3094 (53$^{rd}$ ed., 1999).
Physician's Desk Reference® 3101–3104 (53$^{rd}$ ed., 1999).
Physician's Desk Reference® 3224–3225 (53$^{rd}$ ed., 1999).
Physician's Desk Reference® 3267–3272 (53$^{rd}$ ed., 1999).
Physician's Desk Reference® 3307–3309 (53$^{rd}$ ed., 1999).
Physician's Desk Reference® 3383–3384 (53$^{rd}$ ed., 1999).

Remingtons: The Practice of TheScience and Pharmacy, 19$^{th}$ ed., Gennaro, ed., p. 1625 (1995).

Stock, M.J., Sibutramine: A Review of the Pharmacology of a Novel Anti–Obesity Agent, Int'l J. Obesity, 21(Supp. 1):S25–S29 (1997).

SALTS OF SIBUTRAMINE METABOLITES, METHODS OF MAKING SIBUTRAMINE METABOLITES AND INTERMEDIATES USEFUL IN THE SAME, AND METHODS OF TREATING PAIN

This application is a continuation-in-part of U.S. application Ser. No. 09/372,158, filed Aug. 11, 1999, the entirety of which is incorporated herein by reference.

1. FIELD OF THE INVENTION

The invention relates to compositions comprising dopamine reuptake inhibitors, including racemic and optically pure metabolites of sibutramine, and to methods of making and using the same.

2. BACKGROUND OF THE INVENTION

Sibutramine, chemically named [N-1-[1-(4-chlorophenyl) cyclobutyl]-3-methylbutyl]-N,N-dimethylamine, is a neuronal monoamine reuptake inhibitor which was originally disclosed in U.S. Pat. Nos. 4,746,680 and 4,806,570. Sibutramine inhibits the reuptake of norepinephrine and, to a lesser extent, serotonin and dopamine. See, e.g., Buckett et al., *Prog. Neuro-psychopharm. & Biol. Psychiat.*, 12:575–584, 1988; King et al., *J. Clin. Pharm.*, 26:607–611 (1989).

Racemic sibutramine is sold as a hydrochloride monohydrate under the tradename MERIDIA®, and is indicated for the treatment of obesity. *Physician's Desk Reference®* 1494–1498 (53$^{rd}$ ed., 1999). The treatment of obesity using racemic sibutramine is disclosed, for example, in U.S. Pat. No. 5,436,272.

Sibutramine appears to have been extensively studied, and reportedly could be used in the treatment of a variety of disorders. For example, U.S. Pat. Nos. 4,552,828, 4,746, 680, 4,806,570, and 4,929,629 disclose methods of treating depression using racemic sibutramine, and U.S. Pat. Nos. 4,871,774 and 4,939,175 disclose methods of treating Parkinson's disease and senile dementia, respectively, using racemic sibutramine. Other uses of sibutramine are disclosed by PCT publications WO 95/20949, WO 95/21615, WO 98/11884, and WO 98/13033. Further, the optically pure entantiomers of sibutramine have been considered for development. For example, PCT publications WO 94/00047 and 94/00114 disclose methods of treating depression and related disorders using the (+)-and (−)-enantiomers of sibutramine, respectively.

Sibutramine is rapidly absorbed from the gastrointestinal tract following oral administration and undergoes an extensive first-pass metabolism that yields the primary metabolites, desmethylsibutramine and didesmethylsibutramine, shown below.

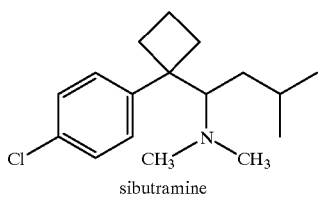
sibutramine

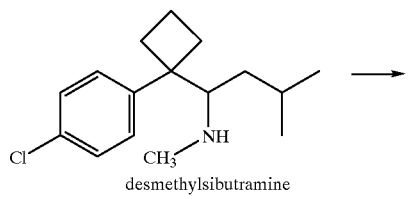
desmethylsibutramine

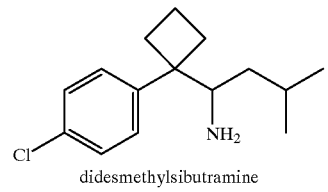
didesmethylsibutramine

It has been reported that desmethylsibutramine and didesmethylsibutramine are more potent in vitro noradrenaline and 5-hydroxytryptamine (5HT; serotonin) reuptake inhibitors than sibutramine. Stock, M. J., *Int'l J. Obesity*, 21(Supp. 1):S25–S29 (1997). It has further been reported, however, that sibutramine and its metabolites have negligible affinities for a wide range of neurotransmitter receptors, including serotonergic (5-HT$_1$, 5-HT$_{1A}$, 5-HT$_{1D}$, 5-HT$_{2A}$, 5-HT$_{2C}$), adrenergic, dopaminergic, muscarinic, histaminergic, glutamate, and benzodiazepine receptors. Id.

Sibutramine has a variety of adverse effects. See, e.g., *Physician's Desk Reference®* 1494–1498 (53$^{rd}$ ed., 1999). Coupled with the reported benefits and therapeutic insufficiencies of sibutramine, this fact has encouraged the discovery of compounds and compositions that can be used in the treatment or prevention of disorders such as, but not limited to, erectile dysfunction, affective disorders, weight gain or obesity, cerebral function disorders, pain, obsessive-compulsive disorder, substance abuse, chronic disorders, anxiety, eating disorders, migraines, and incontinence. In particular, compounds and compositions are desired that can be used for the treatment and prevention of such disorders and conditions while incurring fewer of the adverse effects associated with sibutramine.

3. SUMMARY OF THE INVENTION

This invention encompasses methods, pharmaceutical compositions, and dosage forms for the treatment and prevention of disorders that are ameliorated by the inhibition of neuronal monoamine uptake in mammals, including humans. Examples of such disorders include, but are not limited to, erectile dysfunction, affective disorders, weight gain or obesity, cerebral function disorders, pain, obsessive-compulsive disorder, substance abuse, chronic disorders, anxiety, eating disorders, migraines, and incontinence. The methods of the invention comprise administering to a patient in need of such treatment or prevention a therapeutically or prophylactically effective amount of a racemic or optically pure sibutramine metabolite, or a pharmaceutically acceptable salt, solvate, or clathrate thereof.

This invention also encompasses a method of treating or preventing erectile dysfunction which comprises adjunctively administering to a patient in need of such treatment or prevention therapeutically or prophylactically effective amounts of a dopamine reuptake inhibitor and a 5-HT$_3$ antagonist.

Pharmaceutical compositions of the invention comprise a therapeutically or prophylactically effective amount of a neuronal monoamine reuptake inhibitor. Preferred neuronal monoamine reuptake inhibitors include, but are not limited to, apomorphine, racemic and optically pure sibutramine metabolites, and pharmaceutically acceptable salts, solvates, and clathrate thereof. Pharmaceutical compositions of the invention can further comprise other drug substances, including, but not limited to, 5-HT$_3$ antagonists.

The invention encompasses the use of racemic and optically pure sibutramine metabolites as effective dopamine, serotonin, and norepinephrine reuptake inhibitors. Racemic and optically pure sibutramine metabolites include, but are not limited to, (+)-desmethylsibutramine, (−)-desmethylsibutramine, (±)-desmethylsibutramine, (+)-didesmethylsibutramine, (−)-didesmethylsibutramine, and (±)-didesmethylsibutramine.

4. DETAILED DESCRIPTION OF THE INVENTION

This invention relates to methods and compositions that inhibit the reuptake of neuronal monoamines (e.g., dopamine, serotonin, and norepinephrine). The invention thereby provides a method of treating or preventing a disorder ameliorated by the inhibition of neuronal monoamine reuptake which comprises administering to a patient (i.e., a human) in need of such treatment or prevention a therapeutically or prophylactically effective amount of neuronal monoamine reuptake inhibitor. Preferred neuronal monoamine reuptake inhibitors are racemic and optically pure sibutramine metabolites and pharmaceutically acceptable salts, solvates, and clathrates thereof.

As used herein, the term "treating or preventing disorders ameliorated by inhibition of neuronal monoamine reuptake" means relief from symptoms of conditions associated with abnormal neuronal monoamine levels. Disorders ameliorated by inhibition of neuronal monoamine reuptake include, but are not limited to, erectile dysfunction, affective disorders, weight gain or obesity, cerebral function disorders, pain, obsessive-compulsive disorder, substance abuse, chronic disorders, anxiety, eating disorders, migraines, and incontinence.

A first embodiment of the invention encompasses a method of treating or preventing erectile dysfunction which comprises adjunctively administering to a patient in need of such treatment or prevention therapeutically or prophylactically effective amounts of a dopamine reuptake inhibitor and a 5-HT$_3$ antagonist. Preferred dopamine reuptake inhibitors include, but are not limited to, apomorphine, sibutramine, racemic and optically pure sibutramine metabolites, and pharmaceutically acceptable salts, solvates, and clathrates thereof. Particularly preferred dopamine reuptake inhibitors are racemic and optically pure sibutramine metabolites. Preferred 5-HT$_3$ antagonists are antiemetic agents. Examples of suitable 5-HT$_3$ antagonists include, but are not limited to, granisetron (KYTRIL®), metoclopramide (REGLAN®), ondansetron (ZOFRAN®), renzapride, zacopride, tropisetron, and optically pure stereoisomers, active metabolites, and pharmaceutically acceptable salts, clathrates, and solvates thereof.

In a preferred method of this embodiment, the dopamine reuptake inhibitor is administered transdermally or mucosally (e.g., nasally, sublingually, or buccally). In a more preferred method of this embodiment, the dopamine reuptake inhibitor and the 5-HT$_3$ antagonist are both administered transdermally or mucosally.

A second embodiment of the invention encompasses a method of treating or preventing erectile dysfunction which comprises administering to a patient in need of such treatment or prevention a therapeutically or prophylactically effective amount of a racemic or optically pure sibutramine metabolite, or a pharmaceutically acceptable salt, solvate, or clathrate thereof. In a preferred method of this embodiment, the racemic or optically pure sibutramine metabolite or pharmaceutically acceptable salt, solvate, or clathrate thereof is administered transdermally or mucosally.

A third embodiment of the invention encompasses a method of treating or preventing an affective disorder which comprises administering to a patient in need of such treatment or prevention a therapeutically or prophylactically effective amount of a racemic or optically pure sibutramine metabolite, or a pharmaceutically acceptable salt, solvate, or clathrate thereof. Affective disorders include, but are not limited to, depression (e.g., melancholia), attention deficit disorder (including attention deficit disorder with hyperactivity and attention deficit/hyperactivity disorder), bipolar and manic conditions, dysthymic disorder, and cyclothymic disorder. As used herein, the terms "attention deficit disorder" (ADD), "attention deficit disorder with hyperactivity" (ADDH), and "attention deficit/hyperactivity disorder" (AD/HD), are used in accordance with their accepted meanings in the art. See, e.g., *Diagnostic and Statistical Manual of Mental Disorders*, Fourth Ed., American Psychiatric Association, 1997 (DSM-IV™) and *Diagnostic and Statistical Manual of Mental Disorders*, 3$^{rd}$ Ed., American Psychiatric Association (1981) (DSM-III™).

A preferred method of this embodiment is a method of treating or preventing attention deficit disorder which comprises administering to a patient in need of such treatment or prevention a therapeutically or prophylactically effective amount of a racemic or optically pure sibutramine metabolite, or a pharmaceutically acceptable salt, solvate, or clathrate thereof. In the treatment or prevention of attention deficit disorder, the racemic or optically pure sibutramine metabolite is an optically pure sibutramine metabolite, and more preferably is (−)-desmethylsibutramine or (−)-didesmethylsibutramine.

Another preferred method of this embodiment is a method of treating or preventing depression which comprises administering to a patient in need of such treatment or prevention a therapeutically or prophylactically effective amount of a racemic or optically pure sibutramine metabolite, or a pharmaceutically acceptable salt, solvate, or clathrate thereof. As used herein, the term "treating or preventing depression" means relief from or prevention of the symptoms of depression which include, but are not limited to, changes in mood, feelings of intense sadness, despair, mental slowing, loss of concentration, pessimistic worry, agitation, and self-deprecation. Physical changes can also be relieved or prevented by this method, and include, but are not limited to, insomnia, anorexia, decreased energy and libido, and abnormal hormonal circadian rhythms.

A fourth embodiment of the invention encompasses a method of treating or preventing weight gain or obesity which comprises administering to a patient in need of such treatment or prevention a therapeutically or prophylactically effective amount of a racemic or optically pure sibutramine metabolite, or a pharmaceutically acceptable salt, solvate, or clathrate thereof. As used herein, the term "treating or preventing weight gain or obesity" means reduction of weight, relief from being overweight, relief from gaining weight, or relief from obesity, and prevention from gaining weight, all of which are usually due to unnecessary consumption of food.

A fifth embodiment of the invention encompasses a method of treating or preventing a cerebral function disorder which comprises administering to a patient in need of such treatment or prevention a therapeutically or prophylactically effective amount of a racemic or optically pure sibutramine metabolite, or a pharmaceutically acceptable salt, solvate, or clathrate thereof. Cerebral function disorders include, but are not limited to, senile dementia, Alzheimer's type dementia, memory loss, amnesia/amnestic syndrome, disturbance of consciousness, coma, lowering of attention, speech disorders, Parkinson's disease, Lennox syndrome, autism, epilepsy, hyperkinetic syndrome, and schizophrenia. Cerebral function disorders can be induced by factors including, but not limited to, cerebrovascular diseases, such as cerebral infarction, cerebral bleeding, cerebral arteriosclerosis, cerebral venous thrombosis, and head injuries, and conditions having symptoms selected from the group consisting of disturbances of consciousness, senile dementia, coma, lowering of attention, and speech disorders. As used herein, the term "treating or preventing a cerebral function disorder" means relief from or prevention of one or more symptoms associated with cerebral function disorders.

A sixth embodiment of the invention encompasses a method of treating or preventing pain, including chronic pain and neuropathic pain, which comprises administering to a patient in need of such treatment or prevention a therapeutically or prophylactically effective amount of a racemic or optically pure sibutramine metabolite, or a pharmaceutically acceptable salt, solvate, or clathrate thereof.

A specific embodiment of the invention is directed to a method of treating or preventing neuropathic pain which comprises administering to a patient in need of such treatment or prevention a therapeutically or prophylactically effective amount of a racemic or optically pure sibutramine metabolite, or a pharmaceutically acceptable salt, solvate, or clathrate thereof. Examples of neuropathic pain which can be treated by this method include, but are not limited to: thoracic outlet obstruction syndromes; compression and entrapment neuropathies such as ulnar nerve palsey, carpal tunnel syndrome, peroneal nerve palsey, radial nerve palsey; and Guillain-Barré syndrome. Additional examples of neuropathic pain which can be treated according to this method include pain associated with or resulting from: trauma caused by injury or surgical operation; tumors; bony hyperostosis; casts; crutches; prolonged cramped postures; hemorrhage into a nerve; exposure to cold or radiation; collagen-vascular disorders; metabolic diseases such as diabetes; infectious diseases such as Lyme disease and HIV; toxins such as emetine, hexobarbital, barbital, chlorobutanol, sulfonamides, phenytoin, nitrofurantoin, the vinca alkaloids, heavy metals, carbon monoxide, triorthocresylphosphate, orthodinitrophenol, and other solvents and industrial poisons; autoimmune reactions; nutritional deficiency, and vitamin B deficiency in particular; and metabolic disorders such as hypothyroidism, porphyria, sarcoidosis, amyloidosis, uremia and diabetes. In one particular embodiment of the invention, the neuropathic pain is diabetic peripheral neuropathy.

A seventh embodiment of the invention encompasses a method of treating or preventing an obsessive-compulsive disorder which comprises administering to a patient in need of such treatment or prevention a therapeutically or prophylactically effective amount of a racemic or optically pure sibutramine metabolite, or a pharmaceutically acceptable salt, solvate, or clathrate thereof.

An eighth embodiment of the invention encompasses a method of treating or preventing substance abuse which comprises administering to a patient in need of such treatment or prevention a therapeutically or prophylactically effective amount of a racemic or optically pure sibutramine metabolite, or a pharmaceutically acceptable salt, solvate, or clathrate thereof. As used herein, the term "substance abuse" encompasses the abuse of, and physical and/or psychological addiction to, drugs or alcohol. The term "substance abuse" further encompasses its accepted meaning in the art. See, e.g., DSM-IV™ and DSM-III™.

A preferred method encompassed by this embodiment is a method of treating or preventing cocaine and/or heroin abuse.

A ninth embodiment of the invention encompasses a method of treating or preventing nicotine addiction which comprises administering to a patient in need of such treatment or prevention a therapeutically or prophylactically effective amount of a racemic or optically pure sibutramine metabolite, or a pharmaceutically acceptable salt, solvate, or clathrate thereof. Nicotine addiction includes nicotine addiction of all known forms, such as smoking cigarettes, cigars and/or pipes, and addiction to chewing tobacco.

A tenth embodiment of the invention encompasses a method of eliciting smoking cessation which comprises administering to a patient who smokes tobacco a therapeutically effective amount of a racemic or optically pure sibutramine metabolite, or a pharmaceutically acceptable salt, solvate, or clathrate thereof.

In a preferred method encompassed by this embodiment, the racemic or optically pure sibutramine metabolite or pharmaceutically acceptable salt, solvate, or clathrate thereof is administered orally, mucosally, or transdermally. In a more preferred method, the racemic or optically pure sibutramine metabolite or pharmaceutically acceptable salt, solvate, or clathrate thereof is administered transdermally.

Another preferred method encompassed by this embodiment is a method of eliciting smoking cessation which comprises adjunctively administering to a patient who smokes tobacco therapeutically effective amounts of a racemic or optically pure sibutramine metabolite, or a pharmaceutically acceptable salt, solvate, or clathrate thereof, and nicotine. Preferably, the nicotine and/or racemic or optically pure sibutramine metabolite or pharmaceutically acceptable salt, solvate, or clathrate thereof is administered orally, mucosally, or transdermally. More preferably, the nicotine and/or racemic or optically pure sibutramine metabolite or pharmaceutically acceptable salt, solvate, or clathrate thereof is administered transdermally.

Another method encompassed by this embodiment is a method of treating or preventing weight gain associated with smoking cessation which comprises administering to a patient in need of such treatment or prevention a therapeutically or prophylactically effective amount of a racemic or optically pure sibutramine metabolite, or a pharmaceutically acceptable salt, solvate, or clathrate thereof.

An eleventh embodiment of the invention encompasses a method of treating or preventing a chronic disorder selected from the group consisting of narcolepsy, chronic fatigue syndrome, seasonal affective disorder, fibromyalgia, and premenstrual syndrome (or premenstrual dysphoric disorder). This method comprises administering to a patient in need of such treatment or prevention a therapeutically or prophylactically effective amount of a racemic or optically pure sibutramine metabolite, or a pharmaceutically acceptable salt, solvate, or clathrate thereof.

Preferred methods of this embodiment are methods of treating or preventing premenstrual syndrome, narcolepsy, and chronic fatigue.

A twelfth embodiment of the invention encompasses a method of treating or preventing anxiety which comprises administering to a patient in need of such treatment or prevention a therapeutically or prophylactically effective amount of a racemic or optically pure sibutramine metabolite, or a pharmaceutically acceptable salt, solvate, or clathrate thereof.

A thirteenth embodiment of the invention encompasses a method of treating or preventing an eating disorder which comprises administering to a patient in need of such treatment or prevention a therapeutically or prophylactically effective amount of a racemic or optically pure sibutramine metabolite, or a pharmaceutically acceptable salt, solvate, or clathrate thereof.

A fourteenth embodiment of the invention encompasses a method of treating or preventing a migraine or migraine headache which comprises administering to a patient in need of such treatment or prevention a therapeutically or prophylactically effective amount of a racemic or optically pure sibutramine metabolite, or a pharmaceutically acceptable salt, solvate, or clathrate thereof.

As used herein, the terms "obsessive-compulsive disorder," "pre-menstrual syndrome," "anxiety," "eating disorder," and "migraine" are used consistently with their accepted meanings in the art. See, e.g., DSM-IV™ and DSM-III™. The term "methods of treating or preventing" when used in connection with these disorders means the amelioration, prevention, or relief from symptoms and/or effects associated with these disorders.

A fifteenth embodiment of the invention encompasses a method of treating or preventing incontinence which comprises administering to a patient in need of such treatment or prevention a therapeutically or prophylactically effective amount of a racemic or optically pure sibutramine metabolite, or a pharmaceutically acceptable salt, solvate, or clathrate thereof. In particular, a racemic or optically pure sibutramine metabolite can be used to treat fecal incontinence, stress urinary incontinence ("SUI"), urinary exertional incontinence, urge incontinence, reflex incontinence, passive incontinence and overflow incontinence.

As used herein, the term "treating or preventing incontinence" means treatment, prevention of, or relief from the symptoms of incontinence including involuntary voiding of feces or urine, and dribbling or leakage or feces or urine, which may be due to one or more causes including, but not limited to, pathology altering sphincter control, loss of cognitive function, overdistention of the bladder, hyper-reflexia and/or involuntary urethral relaxation, weakness of the muscles associated with the bladder or neurologic abnormalities.

A preferred method encompassed by this embodiment is a method of treating or preventing stress urinary incontinence. In a further preferred method encompassed by this embodiment, the patient is an elder human of an age greater than 50 or a child of an age less than 13.

Another embodiment of the invention encompasses optically pure sibutramine metabolites such as, but not limited to, (R)-desmethylsibutramine, (S)-desmethylsibutramine, (R)-didesmethylsibutramine, and (S)-didesmethylsibutramine, and pharmaceutically acceptable salts, solvates and clathrates thereof. In particular, this invention encompasses the tartarate, mandelate, and hydrochloride salts of (R)-desmethylsibutramine, (S)-desmethylsibutramine, (R)-didesmethylsibutramine, and (S)-didesmethylsibutramine.

This invention further encompasses compounds of the formula:

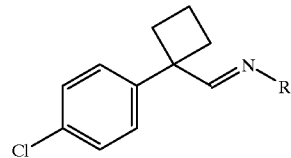

and pharmaceutically acceptable salts, solvates and clathrates thereof, wherein R is alkyl, more preferably $C_1$–$C_6$ alkyl, even more preferably methyl, ethyl, or propyl, and most preferably methyl.

This invention also encompasses the compound of the formula:

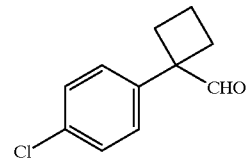

and pharmaceutically acceptable salts, solvates and clathrates thereof.

Another embodiment of the invention encompasses a method of preparing a compound of Formula 2:

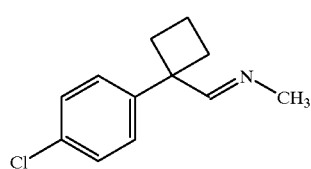

which comprises contacting cyclobutanecarbonitrile with diisobutylaluminum hydride to form an intermediate; and reacting the intermediate with $CH_3NH_2$ at a temperature and for a time sufficient to form the compound of Formula 2.

Another embodiment of the invention encompasses a method of preparing racemic or optically pure desmethylsibutramine which comprises contacting a compound of Formula 2 with a compound of the formula AMX, wherein A is aryl, alkyl, or aralkyl, M is Li or Mg, and X is a halogen atom (e.g., Br or I).

The invention further encompasses a method of preparing optically pure (R)-desmethylsibutramine or a pharmaceutically acceptable salt, solvate or clathrate thereof which comprises contacting racemic desmethylsibutramine with (R)-mandelic acid in a solvent which is or which comprises a mixture of ethyl acetate and heptane to form the (R)-mandelate salt of (R)-desmethylsibutramine.

The invention further encompasses a method of preparing optically pure (S)-desmethylsibutramine or a pharmaceutically acceptable salt, solvate or clathrate thereof which comprises contacting racemic desmethylsibutramine with (S)-mandelic acid in a solvent which is or which comprises a mixture of ethyl acetate and heptane to form the (S)-mandelate salt of (S)-desmethylsibutramine.

The invention further encompasses a method of preparing optically pure (R)-didesmethylsibutramine or a pharmaceutically acceptable salt, solvate or clathrate thereof which comprises contacting racemic didesmethylsibutramine with (R)-mandelic acid in a solvent which is or which comprises a mixture of acetonitrile and methanol to form the (R)-mandelate salt of (R)-didesmethylsibutramine.

The invention further encompasses a method of preparing optically pure (S)-didesmethylsibutramine or a pharmaceutically acceptable salt, solvate or clathrate thereof which comprises contacting racemic didesmethylsibutramine with (S)-mandelic acid in a solvent which is or which comprises a mixture of acetonitrile and methanol to form the (S)-mandelate salt of (S)-didesmethylsibutramine.

Another embodiment of the invention encompasses pharmaceutical compositions and dosage forms comprising a racemic or optically pure sibutramine metabolite or a pharmaceutically acceptable salt, solvate, or clathrate thereof. These pharmaceutical compositions and dosage forms are particularly useful in the methods described above. For example, dosage forms of the invention are suitable for oral, mucosal (e.g., nasal, sublingual, buccal, rectal, and vaginal), parenteral (e.g., intravenous and intramuscular), transdermal, or subcutaneous administration. Preferred dosage forms of the invention are suitable for oral, mucosal, or transdermal administration.

Preferred racemic and optically pure sibutramine metabolites include, but are not limited to, (+)-desmethylsibutramine, (−)-desmethylsibutramine, (±)-desmethylsibutramine, (+)-didesmethylsibutramine, (−)-didesmethylsibutramine, and (±)-didesmethylsibutramine.

Optically pure metabolites of sibutramine are most preferred. As used herein, the term "optically pure" means that a composition contains greater than about 90% of the desired stereoisomer by weight, preferably greater than about 95% of the desired stereoisomer by weight, and more preferably greater than about 99% of the desired stereoisomer by weight, based upon the total weight of the active ingredient. For example, optically pure (+)-desmethylsibutramine is substantially free of (−)-desmethylsibutramine. As used herein, the term "substantially free" means that a composition contains less than about 10 weight percent, preferably less than about 5 weight percent, and more preferably less than about 1 weight percent of a compound.

It is contemplated that pharmaceutically acceptable salts, solvates, and clathrates of racemic and optically pure sibutramine metabolites be used in the methods, pharmaceutical compositions, and dosage forms of the invention. As used herein, the term "pharmaceutically acceptable salt" refers to a salt prepared from a pharmaceutically acceptable non-toxic inorganic or organic acid. Inorganic acids include, but are not limited to, hydrochloric, hydrobromic, hydroiodic, nitric, sulfuric, and phosphoric. Organic acids include, but are not limited to, aliphatic, aromatic, carboxylic, and sulfonic organic acids including, but not limited to, formic, acetic, propionic, succinic, benzoic camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, alginic, and galacturonic acid. Particularly preferred acids are hydrobromic, hydrochloric, phosphoric, and sulfuric acids, and most particularly referred is hydrochloric acid.

In each of the methods of the invention, a sibutramine metabolite or a pharmaceutically acceptable salt, solvate, or clathrate thereof, can be adjunctively administered with one or more additional pharmacologically active compounds, i.e., the sibutramine metabolite and at least one additional pharmacologically active compound are administered as a combination, concurrently but separately, or sequentially by any suitable route (e.g., orally, transdermally, or mucosally).

Further, preferred pharmaceutical compositions and dosage forms of the invention can comprise a pharmaceutically acceptable excipient and/or at least one additional pharmacologically active compound.

Additional pharmacologically active compounds that can be used in the methods and compositions of the invention include, but are not limited to, drugs that act on the central nervous system ("CNS"), such as, but not limited to: 5-HT (e.g., 5-HT$_3$ and 5-HT$_{1A}$) agonists and antagonists; selective serotonin reuptake inhibitors ("SSRIs"); hypnotics and sedatives; drugs useful in treating psychiatric disorders including antipsychotic and neuroleptic drugs, antianxiety drugs, antidepressants, and mood-stabilizers; CNS stimulants such as amphetamines; dopamine receptor agonists; antimonic agents; antipanic agents; cardiovascular agents (e.g., beta blockers and angiotensin converting enzyme inhibitors); antivirals; antibiotics; antifungals; and antineoplastics.

More specific drugs that act on the CNS include, but are not limited to, SSRIs, benzodiazepine compounds, tricyclic antidepressants, antipsychotic agents, anti-anxiolytic agents, β-adrenergic antagonists, 5-HT$_{1A}$ receptor antagonists, and 5-HT$_3$ receptor agonists. Even more specific drugs that act on the CNS include, but are not limited to, lorazepam, tomoxetine, olanzapine, respiradone, buspirone, hydroxyzine, and valium.

Selective serotonin reuptake inhibitors are compounds that inhibit the central nervous system uptake of serotonin while having reduced or limited affinity for other neurologically active receptors. Examples of SSRIs include, but are not limited to, citalopram (CELEXA®); fluoxetine (PROZAC®) fluvoxamine (LUVOX®); paroxetine (PAXIL®); sertraline (ZOLOFT®); venlafaxine (EFFEXOR®); and optically pure stereoisomers, active metabolites, and pharmaceutically acceptable salts, solvates, and clathrates thereof.

Benzodiazepine compounds that can be used in the methods and compositions of the invention include, but are not limited to, those described in Goodman & Gilman, *The Pharmacological Basis of Therapeutics*, 362–373 (9$^{th}$ ed. McGraw-Hill, 1996). Examples of specific benzodiazepines include, but are not limited to, alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, triazolam, pharmacologically active metabolites and stereoisomers thereof, and pharmaceutically acceptable salts, solvates, clathrates thereof. The tradenames of some of these compounds are provided below.

Alprazolam, which is chemically named 8-chloro-1-methyl-6-phenyl-4H-s-triazolo[4,3-α][1,4]benzodiazepine, is sold under the tradename XANAX®. XANAX® is indicated for the management of anxiety disorder (a condition corresponding most closely to the DSM-III™ diagnosis of generalized anxiety disorder) or the short-term relief of symptoms of anxiety. *Physician's Desk Reference®* 2516–2521 (53$^{rd}$ ed., 1999).

The hydrochloride salt of chlordiazepoxide, which is chemically named 7-chloro-2-(methylamino)-5-phenyl-3H-1,4-benzodiazepine 4-oxide hydrochloride, is sold under the tradename LIBRIUM®. LIBRIUM® is indicated for the management of anxiety disorders or for the short-term relief of symptoms of anxiety, withdrawal symptoms of acute alcoholism, and preoperative apprehension and anxiety. *Physician's Desk Reference®* 1369–1370 (53$^{rd}$ ed., 1999).

Clonazepam, which is chemically named 5-(2-chlorophenyl)-1,3-dihydro-7-nitro-2H-1,4-benzodiazepin- 2-one, is sold under the tradename KLONOPIN®. KLONOPIN® is useful alone or as an adjunct in the treatment of the Lennox-Gastaut syndrome (petit mal variant), akinetic and myoclonic seizures. KLONOPIN® is also indicated for the treatment of panic disorder, with or without agoraphobia, as defined in DSM-III™. *Physician's Desk Reference*® 2688–2691 (53$^{rd}$ ed., 1999).

The dipotassium salt of clorazepate, which is chemically named 7-chloro-2,3-dihydro-2,2-dihydroxy-5-phenyl-1H-1,4-benzodiazepine-3-carboxylic dipotassium, is sold under the tradename TRANXENE®. TRANXENE® is indicated for the management of anxiety disorders or for the short-term relief of the symptoms of anxiety, as adjunctive therapy in the management of partial seizures, and for the symptomatic relief of acute alcohol withdrawal. *Physician's Desk Reference*® 475–476 (53$^{rd}$ ed., 1999).

Diazepam, which is chemically named 7-chloro-1,3-dihydro-1-methyl-5-phenyl-2H-1,4-benzodiazepin-2-one, is sold under the tradename VALIUM®. VALIUM® is indicated for the management of anxiety disorders or for the short-term relief of the symptoms of anxiety. *Physician's Desk Reference*® 2735–2736 (53$^{rd}$ ed., 1999).

Estazolam, which is chemically named 8-chloro-6-phenyl-4H-s-triazolo[4-3-α][1,4]benzodiazepine, is sold under the tradename PROSOM™. PROSOM™ is indicated for the short-term management of insomnia characterized by difficulty in falling asleep, frequent nocturnal awakenings, and/or early morning awakenings. *Physician's Desk Reference*® 473–475 (53$^{rd}$ ed., 1999).

Flumazenil, which is chemically named ethyl 8-fluoro-5,6-dihydro-5-methyl-6-oxo-4H-imidazo[1,5-α](1,4)benzodiazepine-3-carboxylate, is sold under the tradename ROMAZICON®. ROMAZICON® is indicated for the complete or partial reversal of the sedative effects of benzodiazepines in cases where general anesthesia has been induced and/or maintained with benzodiazepines, where sedation has been produced with benzodiazepines for diagnostic and therapeutic procedures, and for the management of benzodiazepine overdose. *Physician's Desk Reference*® 2701–2704 (53$^{rd}$ ed., 1999).

The hydrochloride salt of flurazepam, which is chemically named 7-chloro-1-[2-(di-ethylamino)ethyl]-5-(o-fluorophenyl)- 1,3-dihydro-2H-1,4-benzodiazepin-2-one dihydrochloride, is sold under the tradename DALMANE®. DALMANE® is a hypnotic agent useful for the treatment of insomnia characterized by difficulty in falling asleep, frequent nocturnal awakenings, and/or early morning awakenings. *Physician's Desk Reference*® 2520 (52$^{nd}$ ed., 1998).

Lorazepam, which is chemically named 7-chloro-5-(o-chlorophenyl)-1,3-dihydro-3-hydroxy-2H-1,4-benzodiazepin-2-one, is sold under the tradename ATIVAN®. ATIVAN® is indicated for the management of anxiety disorders or for the short-term relief of the symptoms of anxiety or anxiety associated with depressive symptoms. *Physician's Desk Reference*® 3267–3272 (53$^{rd}$ ed., 1999).

The hydrochloride salt of midazolam, which is chemically named 8-chloro-6-(2-fluorophenyl)-1-methyl-4H-imidazo[1,5-α][1,4]benzodiazepine hydrochloride, is sold under the tradename VERSED®. VERSED® is indicated for preoperative sedation/anxiolysis/amnesia and general anesthesia. *Physician's Desk Reference*® 2720–2726 (53$^{rd}$ ed., 1999).

Oxazepam, which is chemically named 7-chloro-1,3-dihydro-3-hydroxy-5-phenyl-2H-1,4-benzodiazepin-2-one, is sold under the tradename SERAX®. SERAX® is indicated for the management of anxiety disorders or for the short-term relief of the symptoms of anxiety. *Physician's Desk Reference*® 3383–3384 (53$^{rd}$ ed., 1999).

Quazepam, which is chemically named 7-chloro-5-(o-fluoro-phenyl)-1,3-dihydro-1-(2,2,2-trifluoroethyl)2H-1,4-benzodiazepine-2-thione, is sold under the tradename DORAL®. DORAL® is indicated for the treatment of insomnia characterized by difficulty in falling asleep, frequent nocturnal awakenings, and/or early morning awakenings. *Physician's Desk Reference*® 2958 (52$^{nd}$ ed., 1998).

Temazepam, which is chemically named 7-chloro-1,3-dihydro-3-hydroxy-1-methyl-5-phenyl-2H-1,4-benzodiazepin-2-one, is sold under the tradename RESTORIL®. RESTORIL® is indicated for the short-term treatment of insomnia. *Physician's Desk Reference*® 2075–2078 (53$^{rd}$ ed., 1999).

Triazolam, which is chemically named 8-chloro-6-(o-chlorophenyl)-1-methyl-4H-s-tria-zolo-[4,3-α][1,4] benzodiazepine, is sold under the tradename HALCION®. HALCION® is indicated for the short-term treatment of insomnia. *Physician's Desk Reference*® 2490–2493 (53$^{rd}$ ed., 1999).

The clinician, physician, or psychiatrist will appreciate which of the above compounds can be used in combination with a racemic or optically pure sibutramine metabolite, or a pharmaceutically acceptable salt, solvate, or clathrate thereof, for the treatment or prevention of a given disorder, although preferred combinations are disclosed herein.

Disorders that can be treated or prevented using a racemic or optically pure sibutramine metabolite, or a pharmaceutically acceptable salt, solvate, or clathrate thereof, in combination with a benzodiazepine such as those listed above include, but are not limited to, affective disorders (e.g., depression), anxiety, eating disorders, and cerebral function disorders such as those described herein.

The invention further encompasses methods of using and pharmaceutical compositions comprising a racemic or optically pure sibutramine metabolite, or a pharmaceutically acceptable salt, solvate, or clathrate thereof, in combination with an antipsychotic agent. Antipsychotic agents are used primarily in the management of patients with psychotic or other serious psychiatric illness marked by agitation and impaired reasoning. These drugs have other properties that possibly are useful clinically, including antiemetic and antihistamine effects and the ability to potentiate analgesics, sedatives, and general anesthetics. Specific antipsychotic drugs are tricyclic antipsychotic drugs, of which there are three subtypes: phenothiazines, thioxanthenes, and other heterocyclic compounds, all of which can be used in the methods and compositions of the invention. See, e.g., Goodman & Gilman, *The Pharmacological Basis of Therapeutics*, 404 (9$^{th}$ ed. McGraw-Hill, 1996).

Specific tricyclic antipsychotic compounds include, but are not limited to, chlorpromazine, mesoridazine, thioridazine, acetophenazine, fluphenazine, perphenazine, trifluoperazine, chlorprothixene, thiothixene, clozapine, haloperidol, loxapine, molindone, pimozide, risperidone, desipramine, pharmacologically active metabolites and stereoisomers thereof, and pharmaceutically acceptable salts, solvates, clathrates thereof. The tradenames of some of these compounds are provided herein.

Chlorpromazine, which is chemically named 10-(3-dimethylaminopropyl)-2-chlorphenothiazine, is sold under the tradename THORAZINE®. THORAZINE® is indicated, inter alia, for the management of manifestations of psychotic disorders. *Physician's Desk Reference*® 3101–3104 (53$^{rd}$ ed., 1999).

The besylate salt of mesoridazine, which is chemically named 10-[2(1-methyl-2-piperidyl)ethyl]-2-methyl-sylfinyl)-phenothiazine, is sold under the tradename SER- ENTIL®. SERENTIL® is indicated in the treatment of schizophrenia, behavioral problems in mental deficiency and chronic brain syndrome, alcoholism, and psychoneurotic manifestations. *Physician's Desk Reference®* 764–766 (53$^{rd}$ ed., 1999).

Perphenazine, which is chemically named 4-[3-(2-chlorophenothiazin-10-yl)propyl-1-piperazineethanol, is sold under the tradename TRILAFON®. TRILAFON® is indicated for use in the management of the manifestations of psychotic disorders and for the control of severe nausea and vomiting in adults. *Physician's Desk Reference®* 2886–2888 (53$^{rd}$ ed., 1999).

Trifluoperazine, which is chemically named 10-[3-(4-methyl-1-piperazinyl)-propyl]-2-(trifluoromethyl)-10H-phenothiazine, is sold under the tradename STELAZINE®. STELAZINE® is indicated for the management of the manifestations of psychotic disorders and for the short-term treatment of generalized non-psychotic anxiety. *Physician's Desk Reference®* 3092–3094 (53$^{rd}$ ed., 1999).

Thiothixene, which is chemically named N,N-dimethyl-9-[3-(4-methyl-1-piperazinyl)-propylidene]thioxanthene-2-sulfonamide, is sold under the tradename NAVANE®. NAVANE® is indicated in the management of manifestations of psychotic disorders. *Physician's Desk Reference®* 2396–2399 (53$^{rd}$ ed., 1999).

Clozapine, which is chemically named 8-chloro-11-(4-methyl-1-piperazinyl)5H-dibenzo[b,e][1,4]diazepine, is sold under the tradename CLOZARIL®. CLOZARIL® is indicated for the management of severely ill schizophrenic patients who fail to respond adequately to standard antipsychotic drug treatment. *Physician's Desk Reference®* 2004–2009 (53$^{rd}$ ed., 1999).

Haloperidol, which is chemically named 4-[4-(p-chlorophenyl)-4-hydroxy-piperidonol-4'-fluorobutyrophenone, is sold under the tradename HALDOL®. HALDOL® is indicated for use in the management of patients requiring prolonged parenteral antipsychotic therapy (e.g., patients with chronic schizophrenia). *Physician's Desk Reference®* 2190–2192 (53$^{rd}$ ed., 1999).

Loxapine, which is chemically named 2-chloro-11-(4-methyl-1-piperazinyl)dibenz[bf][1-4]oxaxepine, is sold under the tradename LOXITANE®. LOXITANE® is indicated for the management of the manifestations of psychotic disorders. *Physician's Desk Reference®* 3224–3225 (53$^{rd}$ ed., 1999).

Molindone, which is chemically named 3-ethyl-6,7-dihydro-2-methyl-5-(morpholinomethyl) indol-4(5H)-one hydrochloride, is sold under the tradename MOBAN®. MOBAN® is indicated for the management of the manifestations of psychotic disorders. *Physician's Desk Reference®* 978–979 (53$^{rd}$ ed., 1999).

Pimozide, which is chemically named, 1-[1-[4,4-bis(4-fluorophenyl)butyl]4-piperidinyl]-1,3-dihydro-2H-benzimidazole-2-one, is sold under the tradename ORAP®. ORAP® is indicated for the suppression of motor and phonic tics in patients with Tourette's Disorder who have failed to respond satisfactorily to standard treatment. *Physician's Desk Reference®* 1054–1056 (53$^{rd}$ ed., 1999).

Risperidone, chemically named 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one, is sold under the tradename RISPERDAL®. RISPERDAL® is indicated for the management of the manifestations of psychotic disorders. *Physician's Desk Reference®* 1432–1436 (53$^{rd}$ ed., 1999).

The hydrochloride salt of desipramine, which is chemically named 5H-Dibenz[bf]azepine-5-propanamine-10,11-dihydro-N-methyl-monohydrochloride, is sold under the tradename NORPRAMIN®. NORPRAMIN® is indicated for the treatment of depression. *Physician's Desk Reference®* 1332–1334 (53$^{rd}$ ed., 1999).

Disorders that can be treated or prevented using a racemic or optically pure sibutramine metabolite, or a pharmaceutically acceptable salt, solvate, or clathrate thereof, in combination with an antipsychotic compound, and particularly a tricyclic antipsychotic compound, include, but are not limited to, affective disorders (e.g., depression), anxiety, eating disorders, and cerebral function disorders (e.g., schizophrenia) such as those described herein.

The invention further encompasses methods of using and pharmaceutical compositions comprising a racemic or optically pure sibutramine metabolite, or a pharmaceutically acceptable salt, solvate, or clathrate thereof, in combination with a 5-HT$_{1A}$ receptor antagonist and/or a 13-adrenergic antagonist. Examples of 5-HT$_{1A}$ receptor antagonists and β-adrenergic antagonists that can be used in the methods and compositions of the invention include, but are not limited to: alprenolol; WAY 100135; spiperone; pindolol; (S)-UH-301; penbutolol; propranolol; tertatolol; a compound of the formula I as disclosed in U.S. Pat. No. 5,552,429, which is incorporated herein by reference; pharmacologically active metabolites and stereoisomers thereof; and pharmaceutically acceptable salts, solvates, clathrates thereof.

Alprenolol, which is chemically named 1-(1-methylethyl)amino-3-[2-(2-propenyl)phenoxy]-2-propanol, is described by U.S. Pat. No. 3,466,325, which is incorporated herein by reference.

WAY 100135, which is chemically named N-(t-butyl)-3-[4-(2-methoxphenyl)-piperazin-1-yl]-2-phenylpropanamide, is described by U.S. Pat. No. 4,988,814, which is incorporated herein by reference. See also, Cliffe et al., *J. Med. Chem.*, 36:1509–1510 (1993).

Spiperone, which is chemically named 8-[4-(4-fluorophenyl)-4-oxobutyl]-1-phenyl-1,3,8-triazaspiro[4,5]decan-4-one), is described by U.S. Pat. Nos. 3,155,669 and 3,155,670, both of which are incorporated herein by reference. See also, Middlmiss et al., *Neurosci. and Biobehav. Rev.*, 16:75–82 (1992).

Pindolol, which is chemically named 4-(2-hydroxy-3-isopropylaminopropoxy)-indole, is described by U.S. Pat. No. 3,471,515, which is incorporated herein by reference. See also, Dreshfield et al., *Neurochem. Res.*, 21(5):557–562 (1996).

(S)-UH-301, which is chemically named (S)-5-fluoro-8-hydroxy-2-dipropylamino-tetralin), is well known to pharmacologists and pharmaceutical chemists. See, e.g., Hillyer et al., *J. Med. Chem.*, 33:1541–44 (1990) and Moreau et al., *Brain Res. Bull.*, 29:901–04 (1992).

Penbutolol, which is chemically named (1-(t-butylamino)-2-hydroxy-3-(2-cyclopentyl-phenoxy) propane), is sold under the tradename LEVATOL®. LEVATOL® is indicated the treatment of mild to moderate arterial hypertension. *Physician's Desk Reference®* 2908–2910 (53$^{rd}$ ed., 1999).

The hydrochloride salt of propranolol, which is chemically named 1-isopropylamino-3-(1-naphthalenyloxy)-2-propanol hydrochloride, is sold under the tradename INDERAL®. INDERAL® is indicated in the management of hypertension. *Physician's Desk Reference®* 3307–3309 (53$^{rd}$ ed., 1999).

Tertatolol, chemically named 8-(3-t-butylamino-2-hydroxypropyloxy)-thiochroman, is described by U.S. Pat. No. 3,960,891, which is incorporated herein by reference.

Disorders that can be treated or prevented using a racemic or optically pure sibutramine metabolite, or a pharmaceutically acceptable salt, solvate, or clathrate thereof, in combination with a 5-HT$_{1A}$ receptor antagonist include, but are not limited to, depression, obsessive-compulsive disorders, eating disorders, hypertension, migraine, essential tremor, hypertrophic subaortic stenosis and pheochromocytoma. A specific disorder that can be treated or prevented is post-traumatic depression disorder.

Disorders that can be treated or prevented using a racemic or optically pure sibutramine metabolite, or a pharmaceutically acceptable salt, solvate, or clathrate thereof, in combination with a β-adrenergic antagonist include, but are not limited to, post myocardial infarction depression. Specific β-adrenergic antagonists include, but are not limited to, S(−)-pindolol, penbutolol, and propranolol.

The invention further encompasses methods of using and pharmaceutical compositions comprising a racemic or optically pure sibutramine metabolite, or a pharmaceutically acceptable salt, solvate, or clathrate thereof, in combination with a non-benzodiazepine or non-tricyclic agents. Examples of such additional pharmacologically active compounds include, but are limited to: olanzapine, buspirone, hydroxyzine, tomoxetine, pharmacologically active metabolites and stereoisomers thereof, and pharmaceutically acceptable salts, solvates, clathrates thereof.

Olanzapine, which is chemically named 2-methyl-4-(4-methyl-1-piperazinyl)-10H-thieno[2,3-b][1,5]benzodiazepine, is sold under the tradename ZYPREXA®. ZYPREXA® is indicated for the management of the manifestations of psychotic disorders. *Physician's Desk Reference*® 1641–1645 (53$^{rd}$ ed., 1999).

The hydrochloride salt of buspirone, which is chemically named 8-[4-[4-(2-pyrimidinyl)-1-piperazinyl]butyl]-8-azaspiro-[4.5]decane-7,9-dione monohydrochloride, is sold under the tradename BUSPAR®. BUSPAR® is indicated for the management of anxiety disorders or the short-term relief of the symptoms of anxiety. *Physician's Desk Reference*® 823–825 (53$^{rd}$ ed., 1999).

The hydrochloride salt of hydroxyzine, which is chemically named 1-(p-chlorobenzhydryl)-4[2-(2-hydroxyethoxy)-ethyl] piperazine dihydrochloride, is sold under the tradename ATARAX®. ATARAX® is indicated for symptomatic relief of anxiety and tension associated with psychoneurosis and as an adjunct in organic disease states in which anxiety is manifested. *Physician's Desk Reference*® 2367–2368 (53$^{rd}$ ed., 1999).

Disorders that can be treated or prevented using a racemic or optically pure sibutramine metabolite, or a pharmaceutically acceptable salt, solvate, or clathrate thereof, in combination with a compound selected from the group consisting of lorazepam, tomoxetine, olanzapine, respiradone, buspirone, hydroxyzine, valium, pharmacologically active metabolites and stereoisomers thereof, and pharmaceutically acceptable salts, solvates, clathrates thereof include, but are not limited to, anxiety, depression, hypertension, and attention deficit disorders.

While all combinations of racemic and optically pure sibutramine metabolites and pharmaceutically acceptable salts, solvates, and clathrate thereof, and one or more above described pharmacologically active compounds can be useful and valuable, certain combinations are particularly preferred. Examples of preferred combinations include those wherein a racemic or optically pure sibutramine metabolite, or a pharmaceutically acceptable salt, solvate, or clathrate thereof, is combined with one of the following:

| | | |
|---|---|---|
| alprazolam; | estazolam; | oxazepam; |
| brotizolam; | flumazenil; | prazepam; |
| chlordiazepoxide; | flurazepam; | quazepam; |
| clobazam; | halazepam; | temazepam; |
| clonazepam; | lorazepam; | triazolam; |
| clorazepate; | midazolam; | chlorpromazine; |
| demoxepam; | nitrazepam; | mesoridazine; |
| diazepam; | nordazepam; | thioridazine; |
| acetophenazine; | pimozide; | propranolol; |
| fluphenazine; | risperidone; | tertatolol; |
| perphenazine; | alprenolol; | desipramine; |
| trifluoperazine; | WAY 100135; | clonidine; |
| chlorprothixene; | spiperone; | olanzapine; |
| thiothixene; | S(−)-pindolol; | methylphenidate; |
| clozapine; | R(+)-pindolol; | buspirone; |
| haloperidol; | racemic pindolol; | hydroxyzine; and |
| loxapine; | (S)-UH-301; | tomoxetine. |
| molindone; | penbutolol; | |

4.1 SYNTHESIS OF SIBUTRAMINE METABOLITES

Racemic sibutramine, desmethylsibutramine, and didesmethylsibutramine can be prepared by methods known to those of ordinary skill in the art. See, e.g., U.S. Pat. No. 4,806,570, which is incorporated herein by reference; *J. Med. Chem.*, 2540 (1993) (tosylation and azide replacement); Butler, D., *J. Org. Chem.*, 36:1308 (1971) (cycloalkylation in DMSO); *Tetrahedron Lett.*, 155–58 (1980) (Grignard addition to nitrile in benzene); *Tetrahedron Lett.*, 857 (1997) (OH to azide); and Jeffery, J. E., et al., *J. Chem. Soc. Perkin. Trans* 1, 2583 (1996). Optically pure enantiomers of sibutramine and its metabolites can also be prepared using techniques known in the art. A preferred technique is resolution by fractional crystallization of diastereomeric salts formed with optically active resolving agents. See, e.g., "Enantiomers, Racemates and Resolutions," by J. Jacques, A. Collet, and S. H. Wilen, (Wiley-Interscience, N.Y., 1981); S. H. Wilen, A. Collet, and J. Jacques, *Tetrahedron*, 2725 (1977); E. L. Eliel *Stereochemistry of Carbon Compounds* (McGraw-Hill, N.Y., 1962); and S. H. Wilen *Tables of Resolving Agents and Optical Resolutions* 268 (E. L. Eliel ed., Univ. of Notre Dame Press, Notre Dame, Ind., 1972).

Because sibutramine, desmethylsibutramine, and didesmethylsibutramine are basic amines, diastereomeric salts of these compounds that are suitable for separation by fractional crystallization are readily formed by addition of optically pure chiral acid resolving agents. Suitable resolving agents include, but are not limited to, optically pure tartaric, camphorsulfonic acid, mandelic acid, and derivatives thereof. Optically pure isomers of sibutramine, desmethylsibutramine, and didesmethylsibutramine can be recovered either from the crystallized diastereomer or from the mother liquor, depending on the solubility properties of the particular acid resolving agent employed and the particular acid enantiomer used. The identity and optical purity of the particular sibutramine or sibutramine metabolite isomer so recovered can be determined by polarimetry or other analytical methods.

4.1.1. Preparation of Racemic and Optically Pure Sibutramine and Salts Thereof Racemic and optically pure sibutramine can be prepared by methylation of racemic (R/S) or optically pure (R or S) desmethylsibutramine (DMS) or dimethylation of didesmethylsibutramine (DDMS) under suitable reaction conditions. An example of this method is shown in Scheme 1.

Scheme 1

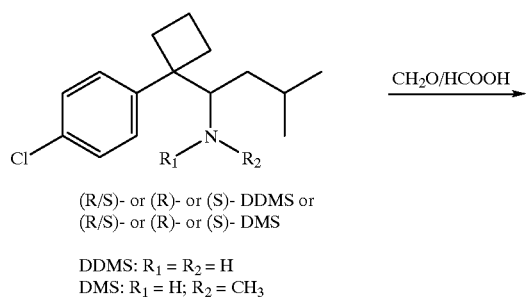

(R/S)- or (R)- or (S)- DDMS or
(R/S)- or (R)- or (S)- DMS

DDMS: $R_1 = R_2 = H$
DMS: $R_1 = H; R_2 = CH_3$

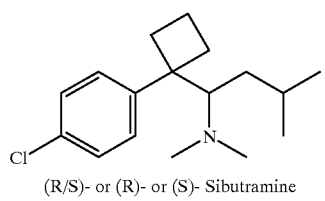

(R/S)- or (R)- or (S)- Sibutramine

According to this method, racemic or optically pure DMS or DDMS is contacted with methylating agent at a sufficient temperature and for a sufficient time to form racemic or optically pure sibutramine, after which time the solvent is removed by conventional means and the product is purified by, for example, crystallization or chromatography. Examples of suitable methylating agents include, but are not limited to, $CH_3X$, wherein X is halogen (e.g., I and Br), and the mixture $CH_2O/HCOOH$. The progress of the reaction can be following using any method known in the art including, for example, thin layer chromatography (TLC) and nuclear magnetic resonance spectroscopy (NMR).

4.1.2. Preparation of Racemic and Optically Pure Desmethylsibutramine and Salts Thereof Racemic desmethylsibutramine can be prepared as shown in Scheme 2:

Scheme 2

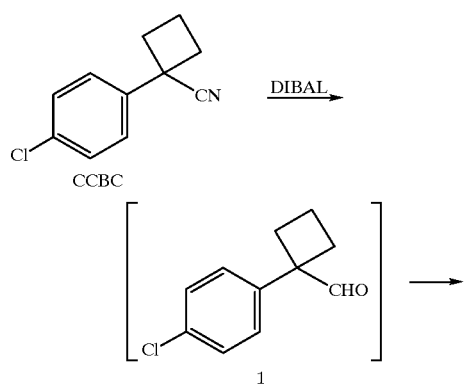

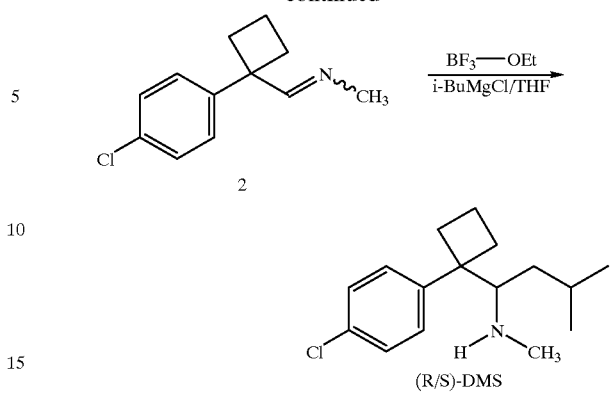

(R/S)-DMS

According to this method, cyclobutanecarbonitrile (CCBC) is reacted with a suitable reducing agent to form a compound of Formula 1. Suitable reducing agents include, but are not limited to, these used in the Stephen and Sonn-Müller reactions (e.g., HCl followed by $SnCl_4$ or $PCl_5$; see J. March, *Advanced Organic Chemistry*, 919 ($4^{th}$ ed: 1992), which is incorporated herein by reference), $LiAlH_4$, $LiAlH(OEt)_3$, $NaAlH_4$, and diisobutylaluminum hydride (DIBAL). Formula 1 is then reacted with an amine to provide a compound of the formula:

wherein R is alkyl (e.g., $C_1$–$C_6$ alkyl, and in particular, methyl, ethyl, or propyl). In the particular method shown in Scheme 2, the compound of Formula 1 is reacted with $CH_3NH_2$ to provide a compound of Formula 2. This reaction is preferably acid catalyzed (e.g., with HCl in water). Formula 2 is then contacted with a metal salt of the isobutyl cation to provide desmethylsibutramine. Examples of metal salts include, but are not limited to, compounds of the formula i-BuMX, wherein X is Br or I and M is selected from the group consisting of Li, Mg, Zn, Cr, and Mn. See J. March, *Advanced Organic Chemistry*, 934–5 ($4^{th}$ ed: 1992), which is incorporated herein by reference. Preferably, the compound is of the formula i-BuMgBr. This reaction can be done in a solvent such as, but not limited to, THF. Preferably, the compound of Formula 2 is contacted with a Lewis acid prior to its reaction with the metal salt. Preferred Lewis acids are selected from the group consisting of $BH_3.THF$, $BF_3.THF$, $BF_3.OEt$, $La(O-i-Pr)_3$, $Zr(O-i-Pr)_4$, $Ti(O-i-Pr)_2Cl_2$, $SnCl_4$, and $MgBr_2.OEt_2$. A particular preferred Lewis acid is $BF_3.OEt$.

The enantiomers of desmethylsibutramine can be resolved by the formation of chiral salts as described herein. Specific preferred chiral acids used to form the chiral salts include, but are not limited to, tartaric and mandelic acids. If tartaric acid is used, preferred solvent systems include, but are not limited to, ethanol/water and isopropyl alcohol/water. If mandelic acid is used, a preferred solvent system is ethyl acetate/hexane.

A method of preparing the hydrochloride salt of racemic desmethylsibutramine ((R/S)-DMS.HCl) is shown in Scheme 3:

Scheme 3

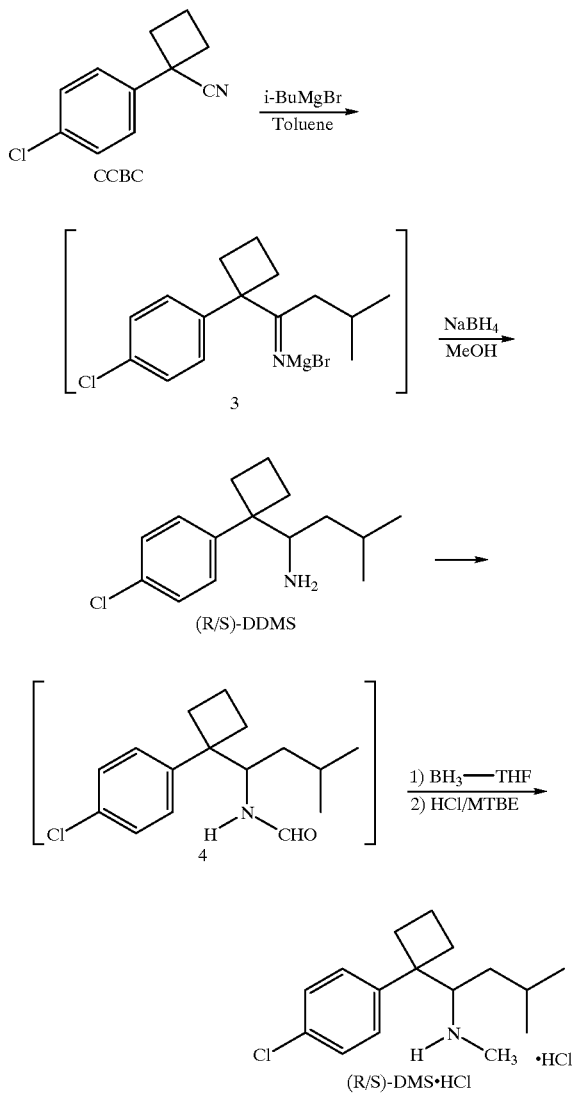

Scheme 4

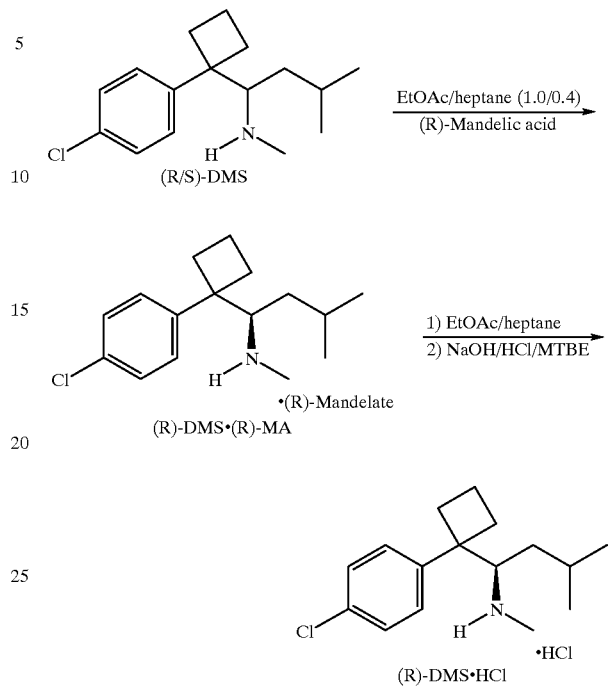

According to this method, CCBC is contacted with a metal salt of the isobutyl cation (e.g., a Grignard reagent) to form an adduct of Formula 3, which is subsequently reduced to form racemic DDMS. Racemic DDMS is then converted to a compound of Formula 4 by, for example, contacting it with formic acid at a suitable temperature and for a suitable time. The compound of Formula 4 is contacted with a reductant such as, but not limited to, $BH_3.THF$, $BF_3.THF$, $BF_3.OEt$, and $LiAlH_4$, and finally and converted to the HCl salt of DMS with the addition of HCl in a suitable solvent such as, but not limited to, t-butyl methyl ether (MTBE).

Optically pure enantiomers of desmethylsibutramine and pharmaceutically acceptable salts, solvate and clathrates are also readily prepared by methods of this invention. For example, the hydrochloride salt of (R)-desmethylsibutramine ((R)-DMS.HCl) can be prepared as shown in Scheme 4:

According to this method, racemic desmethylsibutramine is contacted with a resolving agent such as, but not limited to, (R)-mandelic acid to provide the corresponding salt. A preferred solvent is EtOAc/heptane. The adduct shown in Scheme 4 is the (R)-DMS.(R)-mandelate salt, which is isolated from the mother liquor and subsequently converted to the HCl salt by conventional means, but preferably by dissolving it in EtOAc/heptane followed by base-catalyzed cleavage of the salt and reaction with HCl/MTBE.

The hydrochloride salt of (S)-desmethylsibutramine ((S)-DMS.HCl) can be prepared in an analogous manner, as shown in Scheme 5:

Scheme 5

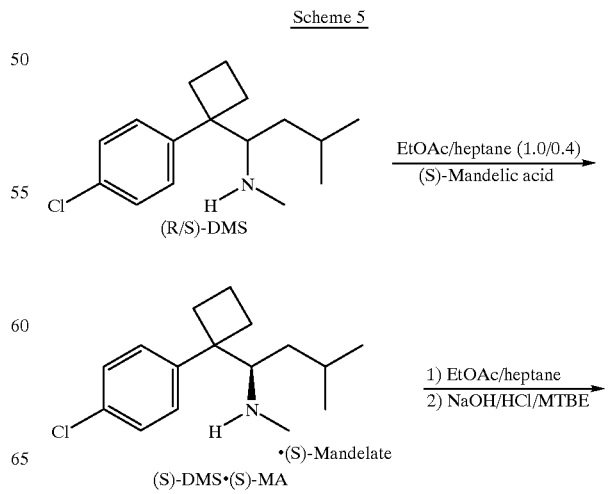

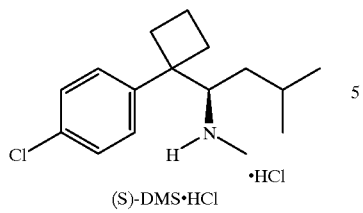

(S)-DMS·HCl

Racemic and optically pure desmethylsibutramine can also be prepared by methylation of didesmethylsibutramine tartarate as shown in Scheme 6.

Scheme 6

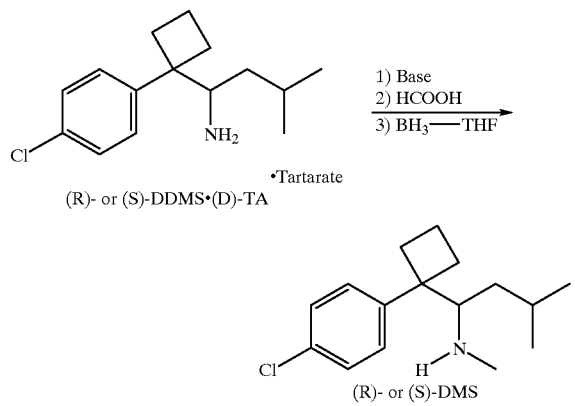

According to this method, HCOOH is reacted with DDMS using base-catalysis to provide a reaction product which is subsequently reduced using a reductant as, but not limited to, BH$_3$·THF.

4.1.3. Preparation of Racemic and Optically Pure Didesmethylsibutramine and Salts Thereof Racemic and optically pure enantiomers of didesmethylsibutramine (DDMS) and pharmaceutically acceptable salts, solvates and clathrates thereof are also readily prepared by methods of this invention. For example, the free base of racemic didesmethylsibutramine ((R/S)-DDMS) can be prepared as shown in Scheme 7.

Scheme 7

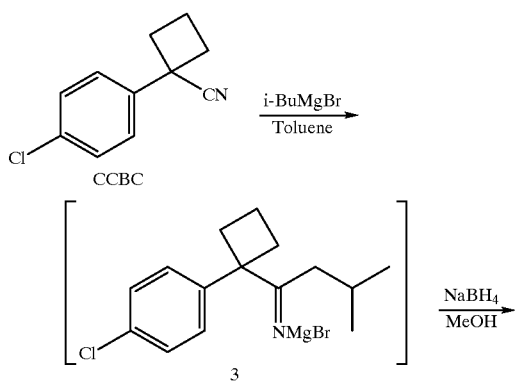

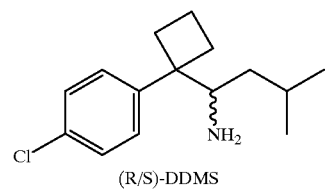

(R/S)-DDMS

According to this method, a compound such as that of Formula 3 is formed by reacting CCBC with a metal salt of the isobutyl cation such as, but not limited to, compounds of a formula i-BuMX, wherein X is Br or I and M is selected from the group consisting of Li, Mg, Zn, Cr, and Mn. Preferably, the compound is of the formula i-BuMgBr. This adduct is subsequently reduced to provide (R/S)-DDMS. Suitable Salts of racemic and optically pure enantiomers of DDMS are readily formed. For example, the (D)-tartrate salt of racemic didesmethylsibutramine ((R/S)-DDMS.(D)-TA) can be prepared as shown below in Scheme 8. It should be noted that the (L)-tartrate salt of racemic didesmethylsibutramine ((R/S)-DDMS.(L)-TA) can be prepared in an analogous manner.

Scheme 8

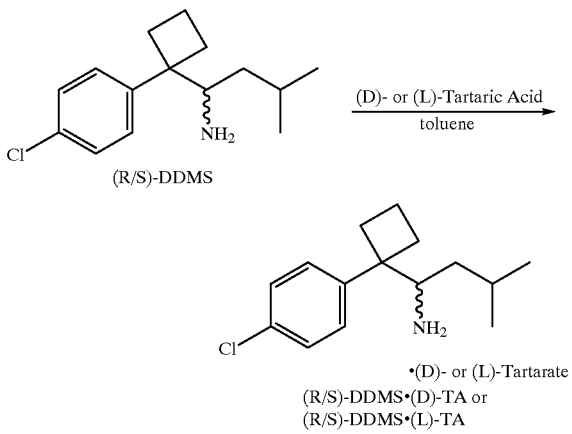

Although any suitable solvent known to those skilled in the art can be used in this method, a preferred solvent is toluene.

The enantiomers of didesmethylsibutramine can be resolved by the formation of chiral salts, as described above. Preferred chiral acids used to form the chiral salts include, but are not limited to, tartaric acid. Preferred solvent systems include, but are not limited to, acetonitrile/water/methanol and acetonitrile/methanol.

The (D)-tartrate salt of optically pure (R)-didesmethylsibutramine ((R)-DDMS.(D)-TA) can be obtained from racemic didesmethylsibutramine free base as shown in Scheme 9:

Scheme 9

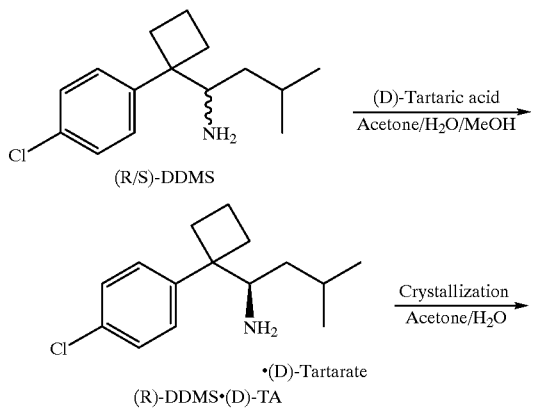

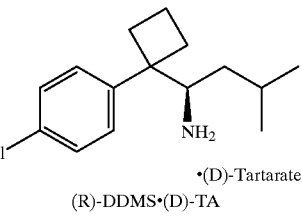

Scheme 11

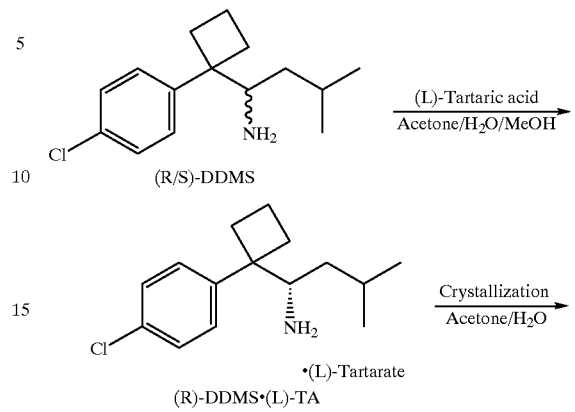

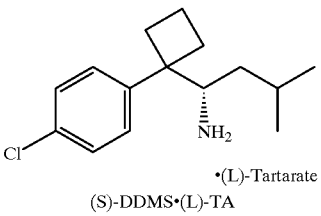

According to this method, racemic DDMS is contacted with (D)-tartaric acid in a suitable solvent. A preferred solvent is a mixture of acetone, water and methanol. The resulting tartarate salt is then isolated from the mother liquor and recrystalized preferably from a mixture of acetone and water to provide (R)-DDMS.(D)-tartarate in high enantiomeric purity.

Alternatively, optically pure ((R)-DDMS.(D)-TA) can be isolated from the tartarate salt of racemic didesmethylsibutramine as shown in Scheme 10.

Scheme 10

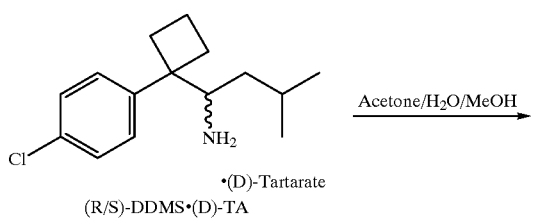

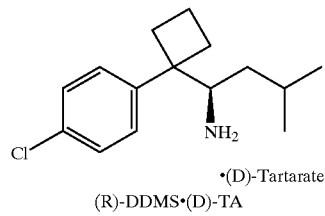

A method of isolating the (L)-tartrate salt of (S)-didesmethylsibutramine ((S)-DDMS.(L)-TA) from racemic didesmethylsibutramine free base is shown in Scheme 11:

According to this method, racemic DDMS is contacted with (L)-tartaric acid in a suitable solvent. A preferred solvent is a mixture of acetone, water and methanol. The resulting tartarate salt is then isolated from the mother liquor and recrystalized preferably from a mixture of acetone and water to provide (S)-DDMS.(L)-tartarate in high enantiomeric purity.

With regard to the resolution of didesmethylsibutramine, it has been found that if tartaric acid is used as a resolving agent, a preferred solvent used during the resolution step is a mixture of acetonitrile, water and methanol ethanol. If mandelic acid is used as a resolving agent, a preferred solvent is a mixture of acetonitrile and methanol.

4.2. PHARMACEUTICAL COMPOSITIONS AND METHODS OF USE

The magnitude of a prophylactic or therapeutic dose of an active ingredient in the acute or chronic management of a disorder or condition will vary with the severity of the disorder or condition to be treated and the route of administration. The dose, and perhaps the dose frequency, will also vary according to age, body weight, response, and the past medical history of the patient. Suitable dosing regimens can be readily selected by those skilled in the art with due consideration of such factors.

Suitable daily doses for the treatment or prevention of a disorder described herein can be readily determined by those skilled in the art. A recommended dose of racemic or optically pure sibutramine metabolite is from about 0.1 mg to about 60 mg per day, given as a single once-a-day dose in the morning or as divided doses throughout the day. Preferably, a daily dose is from about 2 mg to about 30 mg per day, more preferably from about 5 mg to about 15 mg per day.

Suitable daily dosage ranges of additional pharmacologically active compounds that can be adjunctively administered with a racemic or optically pure sibutramine metabolite can be readily determined by those skilled in the art following dosages reported in the literature and recommended in the *Physician's Desk Reference®* (53$^{rd}$ ed., 1999).

For example, suitable daily dosage ranges of 5-HT$_3$ antagonists can be readily determined by those skilled in the art and will vary depending on factors such as those described above and the particular 5-HT$_3$ antagonists used. In general, the total daily dose of a 5-HT$_3$ antagonist for the treatment or prevention of a disorder described herein is from about 0.5 mg to about 500 mg, preferably from about 1 mg to about 350 mg, and more preferably from about 2 mg to about 250 mg per day.

The therapeutic or prophylactic administration of an active ingredient of the invention is preferably initiated at a lower dose, e.g., from about 2 mg to about 8 mg of sibutramine metabolite and optionally from about 15 mg to about 60 mg of 5-HT$_3$ antagonist, and increased, if necessary, up to the recommended daily dose as either a single dose or as divided doses, depending on the global response of the patient. It is further recommended that patients aged over 65 years should receive doses of sibutramine metabolite in the range of from about 5 mg to about 30 mg per day depending on global response. It may be necessary to use dosages outside these ranges, which will be readily determinable by one of ordinary skill in the pharmaceutical art.

The dosage amounts and frequencies provided above are encompassed by the terms "therapeutically effective," "prophylactically effective," and "therapeutically or prophylactically effective" as used herein. When used in connection with an amount of a racemic or optically pure sibutramine metabolite, these terms further encompass an amount of racemic or optically pure sibutramine metabolite that induces fewer or less sever adverse effects than are associated with the administration of racemic sibutramine. Adverse effects associated with racemic sibutramine include, but are not limited to, significant increases in supine and standing heart rate, including tachycardia, increased blood pressure (hypertension), increased psychomotor activity, dry mouth, dental caries, constipation, hypohidrosis, blurred or blurry vision, tension, mydriasis, seizures, formation of gallstones, renal/hepatic dysfunction, fevers, arthritis, agitation, leg cramps, hypertonia, abnormal thinking, bronchitis, dyspnea, pruritus, amblyopia, menstrual disorder, ecchymosis/bleeding disorders, interstitial nephritis, and nervousness. See, e.g., *Physician's Desk Reference®* 1494–1498 (53$^{rd}$ ed., 1999).

Adjunctively administering of two or more active ingredients in accordance with the methods of the invention can be concurrent, sequential, or both. For example, a dopamine reuptake inhibitor and a 5-HT$_3$ antagonist can be administered as a combination, concurrently but separately, or by sequential administration.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Preferred routes of administration include oral, transdermal, and mucosal. As mentioned above, administration of an active ingredient for the treatment or prevention of erectile dysfunction is preferably mucosal or transdermal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose.

A preferred transdermal dosage form is a "reservoir type" or "matrix type" patch, which is applied to the skin and worn for a specific period of time to permit the penetration of a desired amount of active ingredient. For example, if an active ingredient is a sibutramine metabolite, a preferred patch is worn for 24 hours and provides a total daily dose of from about 0.1 mg to about 60 mg per day. Preferably, a daily dose is from about 2 mg to about 30 mg per day, more preferably, from about 5 mg to about 15 mg per day. The patch can be replaced with a fresh patch when necessary to provide constant administration of the active ingredient to the patient.

Other dosage forms of the invention include, but are not limited to, tablets, caplets, troches, lozenges, dispersions, suspensions, suppositories, ointments, cataplasms (poultices), pastes, powders, dressings, creams, plasters, solutions, capsules, soft elastic gelatin capsules, and patches.

In one embodiment, pharmaceutical compositions and dosage forms of the invention comprise a dopamine reuptake inhibitor, such as a racemic or optically pure sibutramine metabolite or a pharmaceutically acceptable salt, solvate, or clathrate thereof, and optionally an additional pharmacologically active compound, such as a 5-HT$_3$ antagonist. Preferred racemic or optically pure sibutramine metabolites are (+)-desmethylsibutramine, (−)-desmethylsibutramine, (±)-desmethylsibutramine, (+)-didesmethylsibutramine, (−)-didesmethylsibutramine, and (±)-didesmethylsibutramine. The pharmaceutical compositions and dosage forms can contain a pharmaceutically acceptable carrier and optionally other therapeutic ingredients known to those skilled in the art.

In practical use, an active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, preferably without employing the use of lactose. For example, suitable carriers include powders, capsules, and tablets, with the solid oral preparations being preferred over the liquid preparations.

Because of their ease of administration, tablets and capsules represent the most advantageous oral dosage unit forms, in which case solid pharmaceutical carriers are employed. If desired, tablets can be coated by standard aqueous or nonaqueous techniques.

In addition to the common dosage forms set out above, an active ingredient can also be administered by controlled release means or delivery devices that are well known to those of ordinary skill in the art, such as those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are incorporated herein by reference. These dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; and 3) increased patient compliance. In addition, controlled-release formulations can be used to affect the time of onset of action or other characteristics, such as blood levels of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various inducers, including, but not limited to, pH, temperature, enzymes, water, or other physiological conditions or compounds.

Pharmaceutical compositions of the invention suitable for oral administration can be presented as discrete dosage forms, such as capsules, cachets, or tablets, or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses lactose-free pharmaceutical compositions and dosage forms. Lactose is used as an excipient in sibutramine formulations. See, e.g., *Physician's Desk Reference®* 1494 ($53^{rd}$ ed., 1999). Unlike the parent drug, however, desmethylsibutramine and didesmethylsibutramine are secondary and primary amines, respectively, and so can potentially decompose over time when exposed to lactose. Thus, compositions of the invention that comprise sibutramine metabolites preferably contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients which are well known in the art and are listed in the USP (XXI)/NF (XVI), which is incorporated herein by reference. In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising an active ingredient, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379–80. In effect, water and heat accelerate decomposition. Thus the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms of racemic or optically pure sibutramine metabolite which contain lactose are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, the invention encompasses a method of preparing a solid pharmaceutical formulation comprising an active ingredient which method comprises admixing under anhydrous or low moisture/humidity conditions the active ingredient and an excipient (e.g., lactose), wherein the ingredients are substantially free of water. The method can further comprise packaging the anhydrous or non-hygroscopic solid formulation under low moisture conditions. By using such conditions, the risk of contact with water is reduced and the degradation of the active ingredient can be prevented or substantially reduced.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pregelatinized starch, hydroxypropyl methyl cellulose, (e.g., Nos. 2208, 2906, 2910), microcrystalline cellulose, and mixtures thereof.

Suitable forms of microcrystalline cellulose include, for example, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.). An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof The binder/filler in pharmaceutical compositions of the present invention is typically present in about 50 to about 99 weight percent of the pharmaceutical composition.

Disintegrants are used in the compositions of the invention to provide tablets that disintegrate when exposed to an aqueous environment. Too much of a disintegrant will produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form the dosage forms of the compounds disclosed herein. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, can be used in the pharmaceutical composition.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pregelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), or mixtures thereof. A lubricant can optionally be added, typically in an amount of less than about 1 weight percent of the pharmaceutical composition.

Dosage forms of the invention that comprise a sibutramine metabolite preferably contain from about 0.1 mg to about 60 mg of the metabolite or pharmaceutically acceptable salt, solvate, or clathrate thereof. For example, each tablet, cachet, or capsule contains from about 0.1 mg to about 60 mg of the active ingredient. Most preferably, the tablet, cachet, or capsule contains either one of three dosages, e.g., about 10 mg, about 20 mg, or about 30 mg of racemic or optically pure sibutramine metabolites (as scored lactose-free tablets, the preferable dose form).

The invention is further defined by reference to the following examples. It will be apparent to those skilled in the art that many modifications, both to materials and methods, can be practiced without departing from the scope of this invention.

5. EXAMPLES

Example 1 describes the preparation of racemic and optically pure sibutramine.

Examples 2–6 describe the preparation of racemic and optically pure forms of desmethylsibutramine (DMS). In each of these examples, the enantiomeric purity of DMS was determined using a Chirobiotic V analytical column (10 $\mu$m, 4.6 mm×25 mm) with 20 mM ammonium acetate/IPA (65:35) as the mobile phase. The UV detector was set to a wavelength of 222 nm.

Examples 7–10 describe the preparation of racemic and optically pure forms of didesmethylsibutramine (DDMS). In each of these examples, the enantiomeric purity of DDMS was determined using an ULTRON ES-OVM analytical column (150 mm×4.6 mm) with 0.01 M $KH_2PO_4$/MeOH (70:30) as the mobile phase. The UV detector was set to a wavelength of 200 nm.

Examples 11–12 describe methods of determining binding affinities of the compounds of the invention and binding affinities measured using those methods.

Finally, Example 13 describes oral formulations comprising compounds of the invention.

5.1. Example 1
SYNTHESIS OF SIBUTRAMINE
Synthesis of 1-(4-Chlorophenyl)cyclobutanecarbonitrile To a suspension of NaH (17.6 g 60%, washed with hexane) in dimethylsulfoxide (150 mL) at room temperature with mechanical stirring was added over a one hour period a mixture of chlorbenzylnitrile (30.3 g) and 1,3-dibromopropane (22.3 mL, 44.5 g). The reaction mixture was stirred for an additional 1 hour, and isopropyl alcohol (10 mL) was added slowly to quench excess NaH. Water (150 mL) was added. The reaction mixture was extracted with t-butyl methyl ether (MTBE) (2×200 mL), and the combined extracts were washed with water (3×200 mL), brine, and dried over $MgSO_4$. The solvent was removed in a rotoevaporator, and the final product was purified by distillation to give the title compound (22 g, 56%) as pale yellow oil, bp 110–120° C./1.0 mm Hg. The product was characterized by $^1$H NMR.

Synthesis of 1-[1-(4-chlorophenyl)cyclobutyl]-3-methylbutylamine

A solution of isobutylmagnesium bromide (2M, 108 mL) in diethyl ether (Aldrich) was concentrated to remove most of the ether. The residue was dissolved in toluene (150 mL), followed by addition of the nitrile made above (22 g). The reaction mixture was heated to 105° C. for 17 hours. The reaction mixture was cooled to room temperature, and added to a slurry of $NaBH_4$ in isopropyl alcohol (450 mL). The reaction mixture was heated under reflux for 6 hours, cooled to room temperature and concentrated. The residue was diluted with water (350 mL), and extracted with ethyl acetate (3×200 mL). The combined extracts were washed with water (100 mL), and dried (MgSO$_4$), and concentrated to give 24.2 g crude product (83%).

Synthesis of Sibutramine Free Base

1-[1-(4-chlorophenyl)cyclobutyl]-3-methylbutylamine (21.6 g) was added to formic acid (27 mL) and aqueous formaldehyde (46 mL). The reaction mixture was heated to 85–95° C. for 18 hours and was cooled to room temperature. 30% NaOH was added until the mixture was basic (pH>11). The solution was extracted with chloroform (3×200 mL) and the extracts were combined and washed with water and brine and concentrated to give 15 g product.

Sibutramine HCl

Sibutramine free base (2.25 g) was dissolved in MTBE (20 mL) and that solution was added to 20 mL 1M HCl in diethyl ether. The reaction mixture was stirred for 30 minutes, and the solid was collected by filtration to give 1.73 g after drying. The product was characterized by $^1$H NMR.

Resolution of Sibutramine 12.3 g racemic sibutramine was dissolved in ethyl acetate (85 mL), and a solution of 21.7 g L-dibenzyltartaric acid ("L-DBTA") in ethyl acetate (85 mL) was added thereto. The reaction mixture was heated to reflux and cooled to room temperature. The white precipitate was collected (ee of salt is ca 85%). The solid was then suspended in 220 mL ethyl acetate and heated at reflux for 30 minutes. The solid was collected to give>95% ee. The salt was further crystallized in isopropyl alcohol (450 mL) to give 11.3 g of salt with>99.3% ee. (−)-Sibutramine L-DBTA (yield 76%). Free base was obtained by treatment of the salt with saturated aqueous NaHCO$_3$ and extracted with chloroform. The (−)-sibutramine HCl salt was obtained with treatment of the free base with HCl/Et$_2$O as described above. Optical rotation of the HCl salt was [α]=3.15 (c=0.9, H$_2$O), $^1$H NMR $^{13}$C (CD$_3$OD), and M$^+$=279. The resolution mother liquor was treated with NaOH to give the partially enriched (+)-sibutramine and was then treated with D-DBTA as described above to give (+)-sibutramine-D-DBTA salt with>99.3% ee. The sibutramine enantiomers were characterized by $^1$H and $^{13}$C NMR: M$^+$=279. The material was also characterized by HPLC and Chiral HPLC.

5.2. Example 2
DESMETHYLSIBUTRAMINE FROM SIBUTRAMINE (−)-Sibutramine (1.25 g) was dissolved in toluene (90 mL) and diethylazo-dicarboxylate ("DEAD") was added (0.8 g, 1.1 eq). The reaction mixture was heated at 50° C. for 6 hours, and 0.8 g DEAD was added. The reaction was heated at 50° C. for another 6 hours, cooled to room temperature and the toluene was removed under vacuum. The residue was suspend in 45 mL of ethanol and 45 mL of saturated aqueous NH$_4$Cl. The reaction mixture was heated under reflux for 3 hours. The reaction mixture was cooled to room temperature and concentrated to remove ethanol. Aqueous NaHCO$_3$ was added until the concentrate was basic. The basic concentrate was extracted with dichloromethane, (3×50 mL). The extracts were combined, dried with sodium sulfate, filtered and concentrated to give a crude product. Flash column chromatography (SiO$_2$) (ethyl acetate/TEA 99:1) gave 0.43 g product. It was characterized by $^1$H and $^{13}$C NMR, M$^+$=266, and optical rotation [α]=−10.6, c=3.3, (CHCl$_3$.) The other enantiomer and racemate were prepared similarly and the isomer was characterized as the (−)-isomer.

Synthesis of desmethylsibutramine hydrochloride isomers

To a solution of (−)-desmethylsibutramine (0.78 g) in ethyl acetate (5 mL) at 0° C. was added HCl/diethyl ether (1 M, 5 mL). The reaction mixture was stirred for 1 hour and the solid was collected by filtration. The solid was then dried to give 0.68 g white solid. The product was characterized by $^1$H and $^{13}$C NMR (DMSO-d$_6$), and a chemical purity of>99% was determined by HPLC. [α]=−5° (c=0.5, H$_2$O). The racemate and the other enantiomer were prepared and characterized in the same way.

5.3. Example 3
(R/S)-DESMETHYLSIBUTRAMINE

Preparation of 1-(4-Chlorophenyl)-1-cyclobutyl carboxaldehyde

Diisobutylaluminum hydride (DIBAL-H) (87 mL, 1M in THF, 87.0 mmol) was added to a solution of 1-(4-chlorophenyl) cyclobutanecarbonitrile (CCBC; 10 g, 52.1 mmol) maintained at −20° C. The resulting mixture was stirred for 4–5 hours at 0° C. and then poured into a 10% aqueous citric acid solution and diluted with 200 mL MTBE. The mixture was stirred at room temperature for 3–4 hours. The aqueous layer was washed with MTBE (1×50 mL) and the combined organic layers were dried over MgSO$_4$ and concentrated to give 9 g (89%) of the above-captioned aldehyde as an oil. $^1$H NMR (CDCl$_3$) δ 9.52 (s, 1H), 7.35–7.06 (m, 4H), 2.77–2.68 (m, 2H), 2.43–2.32 9m, 2H), 2.06–1.89 (m, 2H). $^{13}$C NMR δ 198.9, 139.4, 132.9, 128.9, 127.8, 57.1, 28.3, 15.8.

Preparation of 1-(4-chlorophenyl)-1-cyclobutyl N-methylcarbaimine

A mixture of 1-(4-chlorophenyl)-1-cyclobutyl carboxaldehyde (3 g, 15.4 mmol) and methyl amine (12 mL, 40% aqueous w/w, 154 mmol) was stirred at room temperature for 18–40 hours. The reaction mixture was extracted with MTBE (2×50 mL). The combined organic layers were dried over K$_2$CO$_3$ and concentrated to give 2.5 g (78%) of the above-captioned imine as an oil. $^1$H NMR (CDCl$_3$) δ 7.65 (m, 1H), 7.33–7.11 (m, 4H), 3.34 (s,3H), 2.69–2.44 (m, 2H), 2.44–2.34 (m, 2H), 2.09–1.84 (m, 2H); $^{13}$C NMR δ 168.0, 144.0, 131.8, 128.4, 127.4, 50.6, 47.6, 30.6, 15.8.

Preparation of 1-(4-chlorophenyl)-N-methyl-2-(2-methylpropyl)-cyclobutanamethamine To a solution of 1-(4-chlorophenyl)-1-cyclobutyl N-methylcarbaimine (0.5g, 2.4 mmol) cooled to 0° C. was added BF$_3$.OEt$_2$ (0.34 g, 2.4 mmol). The mixture was stirred for 1 hour and then cooled to −78° C. At this temperature, isobutyl magnesium bromide (2.5 mL, 2M in ether, 5 mmol) was added to form a mixture which was stirred at −78° C. for 2 hours and then warmed to room temperature and stirred overnight. The reaction was quenched with saturated NaHCO$_3$ solution (10 mL) and diluted with MTBE (15 mL). The organic layer was dried over MgSO$_4$, concentrated, and purified by silicagel chromatography (eluting with 1% NEt$_3$ in ethyl acetate) to give 380 mg of the above captioned amine as an oil. $^1$H NMR (CDCl$_3$) δ 7.35–7.19 (m, 4H), 2.65–2.74 (m, 1H), 2.57 (s, 3H), 2.20–2.56 (m, 5H), 1.60–2.00 (m, 3H), 1.20–1.00 (m, 2H), 0.95–0.90 (m, 6H), 0.67–0.60 (m. 1H). $^{13}$C NMR δ 144.7, 131.3, 129.1, 127.4, 65.5, 51.7, 41.4, 37.4, 33.7, 32.3, 25.4, 24.0, 22.0, 16.3.

5.4. Example 4
(R/S)-DESMETHYLSIBUTRAMINE-HCL

Toluene (150 mL) and a solution of CCBC (50.0 g, 261 mmol) in toluene (45 mL) were added to a solution of isobutyl magnesium bromide in THF (392 mL, 1M in THF, 392 mmol). The resulting mixture was distilled until the internal temperature reached 105–110° C. and was then refluxed at this temperature range for 2–4 hours. The reaction mixture was then cooled to 0° C. and quenched with methanol (295 mL). NaBH$_4$ (11 g, 339 mmol) was added portion-wise over 15 minutes to the reaction mixture at 0° C. After stirring for 15 minutes, the reaction mixture was transferred into a 2N aqueous HCl solution (365 mL). The organic phase was distilled until the internal temperature reached 105° C., and was then allowed to cool to room temperature. Formic acid (24 g, 522 mmol) was then added to the reaction mixture, which was then heated to reflux (92–96° C.) for 6–8 hours after which time the reaction mixture was distilled until the internal temperature reached 108° C. The mixture was then cooled to 10° C. and BH$_3$.THF (653 mL, 1.0 M, 653 mmol) was added. The resulting mixture was heated to reflux (69° C.) for 15 hours. The mixture was then cooled to 5° C., combined with methanol (105 mL), and refluxed again for 45 minutes. The reaction mixture was distilled until the internal temperature reached 116° C., and then allowed to cool to 25° C. Hydrochloric acid in MTBE (373 g, 18 wt % of HCl, 1840 mmol) was then added to the mixture to provide a white slurry which was refluxed for 1 hour and then filtered to give 62.3 g (79.0%) of (R/S)-DMS.HCl. NMR (CDCl$_3$): $^1$H (d), 0.85–1.1 (m, 6H), 1.24–1.5 (b, 2H), 1.65–2.14 (b, 4H), 2.2–2.5 (b, 4H), 2.5–2.7 (m, 2H), 3.4–3.6 (b, 1H), 7.3–7.5 (m, 4H), 9.0–9.5 (b, 2H). $^{13}$C (d): 15.5, 21.4, 23.5, 24.7, 31.4, 32.4, 33.2, 35.9, 49.1, 64.2, 128.5, 129.4, 133.0, 141.6.

5.5. Example 5
(R)-DESMETHYLSIBUTRAMINE-HCL
Formation of (R)-Mandelate Salt of (R)-DMS (R/S)-Desmethylsibutramine HCl ((R/S)-DMS.HCl) (60 g) was added to ethyl acetate (300 mL) and the resulting mixture was cooled to 0° C. Aqueous NaOH (1.5 N, 300 mL) was then added to the reaction mixture, which was then stirred for 30 minutes. The organic phase was separated, washed with water (150 mL), and concentrated. (R)-Mandelic acid (30.3 g), ethyl acetate (510 mL total), and heptane (204 mL) were then added to the concentrated organic phase. The resulting mixture was then heated to reflux for 1 hour, after which time it was cooled to 20–23° C. Filtration of the resulting slurry yielded 36.4 g (43.8%) of (R)-desmethylsibutramine-(R)-mandelate ((R)-DMS.(R)-MA; 95.5% ee).

Enrichment of (R)-DMS.(R)-MA

A mixture of (R)-DMS.(R)-MA (30 g, 0.072 mol), ethyl acetate (230 mL), and heptane (230 mL) was heated to reflux for 1 hour. After cooling to 20–23° C., the product was filtered and dried to give 29.6 g (98%) of (R)-DMS.(R)-MA (99.9% ee).

Formation of HCl Salt of (R)-DMS

A mixture of (R)-DMS.(R)-MA (50 g, 0.12 mol), NaOH (100 ml, 3.0 N), and toluene (500 mL) was stirred for 30 minutes. The organic phase was washed with water (200 mL), concentrated to about 300 mL, and cooled to room temperature. HCl/MTBE (100 mL, 14%, 0.34 mol) was then slowly added to the mixture to form (R)-DMS.HCl. After stirring for 30 minutes, the slurry was filtered and the resulting wet cake was washed two times with MTBE and dried to give 34.5 g (95.5%) of (R)-DMS.HCl (99.9% ee; 99.9% chemically pure by NMR). NMR (CDCl$_3$): $^1$H (δ), 0.85–1.1 (m, 6H), 1.24–1.5 (b, 2H), 1.65–2.14 (b, 4H), 2.2–2.5 (b, 4H), 2.5–2.7 (m, 2H), 3.4–3.6 (b, 1H), 7.3–7.5 (m, 4H), 9.0–9.5 (b, 2H), $^{13}$C (δ): 15.5, 21.4, 23.5, 24.7, 31.4, 32.4, 33.2, 35.9, 49.1, 64.2, 128.5, 129.4, 133.0, 141.6.

5.6. Example 6
(S)-DESMETHYLSIBUTRAMINE.HCL
Formation of (S)-Mandelate Salt of (S)-DMS A mixture of (R/S)-DMS.HCl (5.0 g), NaOH (1.5N, 20 mL) and ethyl acetate (50 mL) was stirred for 30 minutes. The organic phase was washed with water (20 mL) and concentrated to give desmethylsibutramine free base (4.2 g, 96%).

Desmethylsibutramine free base (1.1 g, 4.1 mmol) was combined with (S)-mandelic acid (0.62 g, 4.1 mmol), ethyl acetate (11 mL), and heptane (4.4 mL). The resulting mixture was heated to reflux for 30 minutes and cooled to 20–23° C. Filtration of the resulting slurry gave 0.76 g of (S)-desmethylsibutramine.(S)-mandelate salt ((S)-DMS.(S)-MA) (96% ee).

Enrichment of (S)-DMS.(S)-MA

A mixture of (S)-Desmethylsibutramine.(S)-mandelate (0.76 g), ethyl acetate (5 mL), and heptane (5 mL) was heated to reflux for 1 hour. After cooling to 20–23° C., the product was filtered and dried to give 0.72 g (95%) of (S)-DMS.(S)-MA (99.9% ee).

Recovery of (S)-Mandelate Salt of (S)-DMS from Mother Liquor of (S)-DMS.(R)-MA

A solution of (S)-DMS.(R)-MA in ethyl acetate-heptane (67% ee mother liquor) was charged with NaOH (3N, 400 mL) and the reaction mixture was stirred for 30 minutes. The organic phase was washed with water and concentrated. The resulting residue (130 g, 0.49 mol and 67% ee) was charged with (S)-mandelic acid (28.5 g, 0.49 mol), ethyl acetate (1400 mL), and heptane (580 mL). The mixture was heated to reflux for 1 hour and then slowly cooled to room temperature. The resulting slurry was filtered and dried to give 147 g (86% based on (S)-isomer) of (S)-DMS.(S)-MA (99.9% ee).

Formation of HCl Salt of (S)-DMS (S)-Desmethylsibutramine.(S)-mandelate (20 g, 0.048 mol) was added to a mixture of NaOH (60 ml, 3.0 N) and toluene (200 mL). The mixture was stirred for 30 minutes and the organic phase was then washed with water (100 mL), concentrated to about 100 mL, and cooled to room temperature. Hydrochloric acid in MTBE (40 mL, 14%, 0.13 mol) was then added slowly to the mixture to form (S)-DMS.HCl. After stirring for 30 minutes, the slurry was filtered and the resulting wet cake was washed two times with MTBE and dried to give 14 g (96.7%) of (S)-DMS.(L)-MA (99.9% ee; 99.9% chemical purity). NMR (CDCl$_3$): $^1$H (δ), 0.84–1.1 (m, 6H), 1.25–1.5 (b, 2H), 1.65–2.15 (b, 4H), 2.2–2.5 (b, 4H), 2.5–2.7 (m, 2H), 3.4–3.6 (b, 1H), 7.3–7.5 (m, 4H), 9.0–9.5 (b, 2H). $^{13}$C (δ): 15.5, 21.4, 23.5, 24.7, 31.4, 32.4, 33.2, 35.9, 49.1, 64.2, 128.5, 129.4, 133.0, 141.6.

5.7. Example 7
(R/S)-DIDESMETHYLSIBUTRAMINE

A 1 L three-necked round bottom flask was charged with isobutyl magnesium bromide (200 mL, 2.0 M in diethyl ether) and toluene (159 mL) and the resulting mixture was distilled to remove most of the ether. After the mixture was cooled to 20° C., CCBC (50.0 g ) in toluene (45 mL) was added, and resulting mixture was refluxed for 2–4 hours. The reaction mixture was then cooled to 0° C. and methanol (300 mL) was added to it, followed slowly by NaBH$_4$ (11 g). The resulting mixture was then stirred at about 0–10° C. for 15 minutes. The reaction mixture was then added slowly to an aqueous HCl solution (365 mL, 2N) kept at 0° C., and the resulting mixture was warmed to room temperature with continual stirring. After separation of the organic phase, the aqueous phase was washed with toluene (200 mL). The combined organic phases were washed with water (200 mL)

and concentrated to give (R/S)-DDMS (55 g, 85%). NMR (CDCl$_3$): $^1$H ($\delta$), 0.6–0.8 (m, 1H), 0.8–1.0 (m, 6H), 1.1–1.3 (m, 1H), 1.6–2.6 (m, 7H), 3.0–3.3 (m, 1H), 7.0–7.6 (m, 4H), $^{13}$C ($\delta$): 15.4, 21.5, 24.3, 24.7, 31.5, 31.9, 41.1, 50.73, 56.3, 127.7, 129, 131.6, 144.2.

5.8. Example 8
(R/S)-DIDESMETHYLSIBUTRAMINE.(D)-TARTRATE

A mixture of racemic didesmethylsibutramine (15.3 g ) and toluene (160 mL) was heated to 70–80° C. and (D)-tartaric acid (9.1 g) in water (20 mL) and acetone (10 mL) was added slowly. The resulting mixture was refluxed for 30 minutes, after which the water and acetone were removed by distillation. The resulting mixture was cooled to room temperature to provide a slurry which was then filtered. The resulting wet cake was washed two times with MTBE (20 mL×2) and dried to yield (R/S)-DDMS.(D)-TA (22.5 g, 98%). NMR (DMSO): $^1$H ($\delta$), 0.6–0.92 (m, 6H), 0.92–1.1 (m, 1H), 1.1–1.3 (m, 1H), 1.5–1.8 (m, 2H), 1.8–2.1 (m, 1H, 2.1–2.4 (m, 3H), 2.4–2.6 (m, 1H), 3.4–3.6 (m, 1H), 3.9–4.2 (s, 2H), 6.4–7.2 (b, 6H, OH, COOH and NH$_2$), 7.3–7.6 (m, 4H). $^{13}$C ($\delta$): 15.5, 2.1, 23.3, 23.7, 31.5, 31.8, 37.7, 39.7, 54.5, 72.1, 128, 129.7, 131.3, 142.2, 174.6.

5.9. Example 9
(R)-DIDESMETHYLSIBUTRAMINE.(D)-TARTRATE
Resolution from Didesmethylsibutramine Free Base A mixture of (R/S)-didesmethylsibutramine (20.3 g), acetone/water/methanol (350 mL, 1:0.13:0.7, v:v:v), and (D)-tartaric acid (12.1 g) were added to a 500 mL three-necked round bottom. The reaction mixture was heated to reflux for 30 minutes and then cooled to 45° C. The reaction mixture was then seeded with (R)-DDMS.(D)-TA (10 mg; 99.6% ee) and stirred at 40–45° C. for 30 minutes. The mixture was then cooled to room temperature and stirred for 1 hour. The resulting slurry was then filtered and the wet cake was washed with cold acetone/water and dried to give 10.3 g (33%) of (R)-DDMS.(D)-TA (90% ee).
Resolution from (R/S)-Didesmethylsibutramine.(D)-tartrate A mixture of (R/S)-didesmethylsibutramine.(D)-TA (5.0 g) in acetone (50 mL), water (6.7 mL), and methanol (3.3 mL) was refluxed for 30 minutes. The mixture was then cooled to room temperature and the resulting slurry was filtered to provide a wet cake which was then washed with cold acetone and dried to give (R)-DDMS.(D)-TA (1.4 g, 28%; 92% ee).
Enrichment of (D)-Tartrate Salt of (R)-DDMS A mixture of (R)-DDMS.(D)-TA (25 g, 92% ee) and acetonitrile/water/ethanol (300 mL:65 mL:30 mL) was refluxed for 1 hour. The mixture was then cooled to room temperature to provide a slurry which was filtered and dried to give (R)-DDMS.(D)-TA (18 g, 71.3%; 99.7% ee; and 99.91% chemical purity). NMR (DMSO-d$_6$): $^1$H ($\delta$), 0.7–0.9 (m,6H), 0.9–1.05 (t, 1H), 1.1–1.24 (b, 1H), 1.5–1.8 (b, 2H), 1.8–2.02 (b, 1H), 2.1–2.4 (3, 3H), 2.4–2.6 (b, 1H), 3.5 (m, 1H), 4.0 (s, 2H), 7.1–7.6 (m, 4H, with 6H from NH$_2$, OH and COOH). $^{13}$C ($\delta$): 15.4, 21.5, 22.0, 22.2, 32.0, 32.2, 38.4, 49.0, 54.0, 72.8, 128.8, 130.0, 132.0, 143.0, 175.5.

5.10. Example 10
(S)-DIDESMETHYLSIBUTRAMINE.(L)-TARTRATE
Formation of (L)-Tartrate Salt of (S)-DDMS (R/S) Didesmethylsibutramine (20.5 g), acetone/water/methanol (350 mL, 1:0.13:0.7, v:v:v) and (L)-tartaric acid (12.2g) were added to a 500 mL three-necked round bottom flask. The mixture was heated to reflux for 30 minutes and then cooled to 45° C. The reaction mixture was then seeded with (S)-DDMS.(L)-TA (10 mg and 99.7% ee) and stirred at 40–45° C. for 30 minutes. The mixture was cooled to room temperature and stirred for 1 hour. The resulting slurry was filtered to provide a wet cake, which was washed with cold acetone/water and dried to give 10.8 g (33.4%) of (S)-DDMS.(L)-TA (89.7% ee).
Preparation of (L)-Tartrate Salt of (S)-DDMS from Mother Liquor of (R)-DDMS.(D)-TA A solution of DDMS tartrate in acetone/water/methanol (mother liquor of (R)-DDMS.(D)-TA) was concentrated to remove acetone and methanol. The residue was treated with aqueous NaOH (3N, 150 mL) and extracted with ethyl acetate. The organic phase was washed with water (100 mL) and concentrated to give didesmethylsibutramine free base (45 g, 0.18 mol and 36% ee of (S)-isomer). The free amine was charged with (L)-tartaric acid (53.6 g, 0.35 mol), acetone (600 mL), water (80 mL), and methanol (40 mL). The mixture was heated to reflux for 1 hour and then cooled to room temperature. The resulting slurry was filtered to provide a wet cake, which was then washed with cold acetone/water two times to give 26.7 g (56% based on (S)-didesmethylsibutramine) of (S)-DDMS.(L)-TA (96% ee).
Enrichment of (S)-DDMS.(L)-TA A mixture of(S)-DDMS.(L)-TA (26.7 g) in acetonitrile/water (475 mL; 1:0.2, v:v) was refluxed for 1 hour and then cooled to room temperature. The resulting slurry was filtered and dried to give 17.4 g (65%) of (S)-DDMS.(L)-TA (99.9% ee; 99.94% chemical purity). NMR (DMSO-d6): $^1$H ($\delta$), 0.7–0.9 (m, 6H), 0.9–1.05 (m, 1H), 1.1–1.3 (b, 1H), 1.52–1.8 (b, 2H), 1.84–2.05 (b, 1H), 2.15–2.4 (b, 3H), 2.4–2.6 (b, 1H), 3.65–3.58 (m, 1H), 4.0 (s, 2H), 6.7–7.3 (b, 6H from NH$_2$, OH and COOH) 7.1–7.6 (m, 4H). $^{13}$C ($\delta$): 15.4, 21.5, 22.0, 22.2, 32.0, 32.2, 38.4, 49.0, 54.0, 72.8, 128.8, 130.0, 132.0, 143.0, 175.5.

5.11. Example 11
DETERMINATION OF POTENCY AND SPECIFICITY

A pharmacologic study is conducted to determine the relative potency, comparative efficacy, binding affinity, and toxicity of the racemic mixture of sibutramine, its enantiomers, the metabolites of sibutramine, and their enantiomers. The profile of relative specificity of monoamine reuptake inhibition is determined from the compounds' inhibition of norepinephrine (NE) reuptake in brain tissue with that of the inhibition of dopamine (DA) and serotonin (5-HT) reuptake.

High-affinity uptake of the $^3$H-radiomonoamines is studied in synaptosomal preparations prepared from rat corpus striatum (for inhibition of DA reuptake) and cerebral cortex (for 5HT and NE) using methods published by Kula et al., *Life Sciences* 34(26): 2567–2575, 1984, and Baldessarini et al., *Life Sciences* 39:1765–1777, 1986. Tissues are freshly dissected on ice and weighed. Following homogenization by hand (14 strokes in 10–35 vols of ice-cold isotonic 0.32M sucrose, containing nialamide, 34 $\mu$M) in a Teflon-on-glass homogenizer, the tissue is centrifuged for ten minutes at 900 ×g; the supernatant "solution" that results contains synaptosomes that are used without further treatment. Each assay tube contains 50 $\mu$L of the cerebral homogenate, radiolabelled-$^3$H-monoamine, and the test compound (e.g., the pure sibutramine enantiomers, the racemate, and appropriate standards) in a freshly prepared physiologic buffer solution with a final volume of 0.5 mL. Tissues are preincubated for 15 minutes at 37° C. before the assay. Tubes are held on ice until the start of incubation, which is initiated by adding $^3$H-amine to provide a final concentration of 0.1 $\mu$M. Tubes are incubated at 37° C. for 10 minutes with $^3$H-DA (26 Ci/mmol) and for 20 minutes with $^3$H-5HT (about 20 Ci/mmol) and $^3$H-NE (about 20 Ci/mmol). The specific activity of the radiomonoamine will vary with available material and is not critical. The reaction is terminated by immersion in ice and dilution with 3 mL of ice cold isotonic saline solution containing 20 mM TRIS buffer (pH 7.0). These solutions are filtered through cellulose ester microfilters, followed by washing with two 3 mL volumes of the same buffer. The filter is then counted for $^3$H-radioactivity in 3.5 mL of Polyfluor at about 50% efficiency for tritium. Blanks (either incubated at 0° C. or incubated with specific, known uptake inhibitors of DA [GRB-12909, 10 $\mu$M], 5HT- [zimelidine 10 $\mu$M], or of NE [desipramine 10 $\mu$M]) are usually indistinguishable from assays performed without tissue and average 2–3% of total CPM.

Comparison of the amounts of $^3$H-radioactivity retained on the filters provides an indication of the relative abilities of the pure enantiomers and racemic mixture of sibutramine (and of known DA, 5-HT, and NE reuptake inhibitors) to block the reuptake of these monoamines in those tissues. This information is useful in gauging the relative potency and efficacy of compounds of the invention (e.g., dopamine reuptake inhibitors, such as a racemic or optically pure sibutramine metabolite, and 5-HT$_3$ antagonists).

The acute toxicities of the compounds of the invention are determined in studies in which rats are administered progressively higher doses (mg/kg) of the pure isomers or racemate. That lethal dose which, when administered orally, causes death of 50% of the test animals, is reported as the LD$_{50}$. Comparison of LD$_{50}$ values for the enantiomers and racemate provides a measure of the relative toxicity of the compositions.

5.12. Example 12
BINDING AFFINITIES

The binding affinities of racemic and optically pure sibutramine (($\pm$)-, (+)-, and ($-$)-sibutramine), desmethylsibutramine (($\pm$)-, (+)-, and ($-$)-desMe), and didesmethylsibutramine (($\pm$)-, (+)-, and ($-$)-didesMe) were determined at the nonselective muscarinic receptor and the serotonin (5-HT) uptake site from rat cerebral cortex, the human recombinant norepinephrine (NE) uptake site, and the $\beta_3$-receptor from rat adipose tissue. Compounds were tested initially at 10 $\mu$m in duplicate, and if $\geq$50% inhibition of specific binding was observed, they were tested further at 10 different concentrations in duplicate in order to obtain full competition curves. IC$_{50}$ values (concentration required to inhibit 50% specific binding) were then determined by nonlinear regression analysis of the curves and tabulated below.

| Compound | Binding IC$_{50}$ Values (nM) | | | |
| --- | --- | --- | --- | --- |
| | Muscarinic Receptor | NE Uptake | 5-HT Uptake | 5-HT Selectivity (NE/5-HT) |
| ($\pm$)-Sibutramine | 2,650 | 350 | 2,800 | 1,200 |
| (+)-Sibutramine | 4,010 | 110 | 2,100 | 650 |
| ($-$)-Sibutramine | 3,020 | 2,500 | 4,900 | 1,500 |
| ($\pm$)-desMe | 1,170 | 10 | 21 | 19 |
| (+)-desMe | — | 4 | 44 | 12 |
| ($-$)-desMe | 654 | 870 | 9,200 | 180 |
| ($\pm$)-didesMe | — | 16 | 63/14 | 39/26 |
| (+)-didesMe | — | 13 | 140 | 8.9 |
| ($-$)-didesMe | — | 6.2 | 4,300 | 12 |
| Atropine | 0.31 | — | — | — |
| GBR 1909 | — | — | — | 5.6/2.6 |
| Imipramine | — | — | 145/32 | — |
| Protriptyline | — | 3.6/0.9 | — | — |
| Zimelidine | — | — | 129 | — |

None of the compounds showed more than 15% inhibition of binding at the $\beta_3$-receptor, and affinity for the muscarinic site was weak compared to atropine. Further, binding to the NE and 5-HT uptake sites was orders of magnitude less than that of the standards.

The above data, which was generated as described above in Example 13, shows that (+)-desmethylsibutramine and (+)-didesmethylsibutramine are potent inhibitors of NE uptake and 5-HT uptake, but have negligible activity at muscarinic receptors.

5.13. Example 13
ORAL FORMULATION

Hard gelatin capsule dosage forms that are lactose-free comprising sibutramine metabolites can be prepared using the following ingredients:

| Component | 5 mg capsule | 10 mg capsule | 20 mg capsule |
| --- | --- | --- | --- |
| Racemic or optically pure sibutramine metabolite | 5.0 | 10.0 | 20.0 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The racemic or optically pure sibutramine metabolite is sieved and blended with the excipients listed. The mixture is filled into suitably sized two-piece hard gelatin capsules using suitable machinery and methods well known in the art. See, e.g., *Remington's Pharmaceutical Sciences*, 16th or 18th Editions, each incorporated herein in its entirety by reference. Other doses can be prepared by altering the fill weight and, if necessary, changing the capsule size to suit. Any of the stable, non-lactose hard gelatin capsule formulations above can be formed.

Compressed tablet dosage forms of sibutramine metabolites can be prepared using the following ingredients:

| Component | 5 mg capsule | 10 mg capsule | 20 mg capsule |
| --- | --- | --- | --- |
| Racemic or optically pure sibutramine metabolite | 5.0 | 10.0 | 20.0 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The racemic or optically pure sibutramine metabolite is sieved through a suitable sieve and blended with the non-lactose excipients until a uniform blend is formed. The dry blend is screened and blended with the magnesium stearate. The resulting powder blend is then compressed into tablets of desired shape and size. Tablets of other strengths can be prepared by altering the ratio of the active ingredient to the excipient(s) or modifying the table weight.

The embodiments of the invention described above are intended to be merely exemplary and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A compound of the formula:

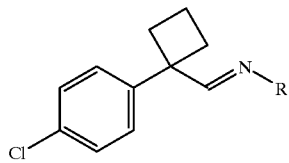

and pharmaceutically acceptable salts, solvates and clathrates thereof, wherein R is alkyl.

2. The compound of claim 1 wherein alkyl is $C_1$–$C_6$ alkyl.

3. The compound of claim 2 wherein the $C_1$–$C_6$ alkyl is methyl.

4. A method of preparing a compound of Formula 2:

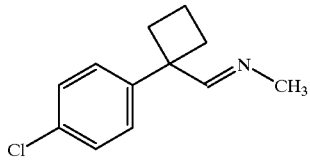

which comprises contacting cyclobutanecarbonitrile with diisobutylaluminum hydride to form an intermediate; and reacting the intermediate with $CH_3NH_2$ at a temperature and for a time sufficient to form the compound of Formula 2.

5. A method of preparing racemic or optically pure desmethylsibutramine which comprises contacting a compound of Formula 2 with a compound of the formula AMX, wherein A is aryl, alkyl, or aralkyl, M is Li or Mg, and X is a halogen atom.

* * * * *

UNITED STATES PATENT AND TRADEMARK OFFICE
CERTIFICATE OF CORRECTION

PATENT NO.    : 6,399,826 B1
DATED         : June 4, 2002
INVENTOR(S)   : Senanayake et al.

It is certified that error appears in the above-identified patent and that said Letters Patent is hereby corrected as shown below:

<u>Title page,</u>
Item [54], Title, please correct the title to read: -- SALTS OF SIBUTRAMINE METABOLITES AND METHODS OF MAKING THE SAME --.

Signed and Sealed this

Twenty-second Day of October, 2002

*Attest:*

*Attesting Officer*

JAMES E. ROGAN
*Director of the United States Patent and Trademark Office*